(12) United States Patent
Jiang et al.

(10) Patent No.: US 11,660,266 B2
(45) Date of Patent: May 30, 2023

(54) METHODS AND COMPOSITIONS FOR SUSTAINED RELEASE MICROPARTICLES FOR OCULAR DRUG DELIVERY

(71) Applicant: Ohio State Innovation Foundation, Columbus, OH (US)

(72) Inventors: Pengfei Jiang, Columbus, OH (US); Katelyn Elizabeth Reilly, Columbus, OH (US); Matthew Ohr, Powell, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 84 days.

(21) Appl. No.: 17/046,639

(22) PCT Filed: Apr. 11, 2019

(86) PCT No.: PCT/US2019/027105
§ 371 (c)(1),
(2) Date: Oct. 9, 2020

(87) PCT Pub. No.: WO2019/200181
PCT Pub. Date: Oct. 17, 2019

(65) Prior Publication Data
US 2021/0145736 A1 May 20, 2021

Related U.S. Application Data

(60) Provisional application No. 62/656,199, filed on Apr. 11, 2018.

(51) Int. Cl.
*A61K 9/00* (2006.01)
*A61K 9/51* (2006.01)
*C07K 16/22* (2006.01)

(52) U.S. Cl.
CPC .......... *A61K 9/0048* (2013.01); *A61K 9/0019* (2013.01); *A61K 9/5146* (2013.01); *A61K 9/5161* (2013.01); *C07K 16/22* (2013.01); *C07K 2317/24* (2013.01)

(58) Field of Classification Search
CPC .. A61K 9/0048; A61K 9/0019; A61K 9/5146; A61K 9/5161; C07K 16/22; C07K 2317/24; A61P 27/02
See application file for complete search history.

(56) References Cited

U.S. PATENT DOCUMENTS

| | | |
|---|---|---|
| 5,138,069 A | 8/1992 | Carini et al. |
| 5,196,444 A | 3/1993 | Naka et al. |
| 5,200,534 A | 4/1993 | Rao |
| 5,202,448 A | 4/1993 | Carver et al. |
| 5,229,529 A | 7/1993 | Ueno et al. |
| 5,270,317 A | 12/1993 | Bernhart et al. |
| 5,274,137 A | 12/1993 | Nicolaou et al. |
| 5,279,949 A | 1/1994 | Nair |
| 5,283,253 A | 2/1994 | Holton et al. |
| 5,294,637 A | 3/1994 | Chen et al. |
| 5,399,578 A | 3/1995 | Buehlmayer et al. |
| 5,415,869 A | 5/1995 | Straubinger et al. |
| 5,440,056 A | 8/1995 | Klein et al. |
| 5,705,517 A | 1/1998 | Naka et al. |
| 5,821,263 A | 10/1998 | Scola et al. |
| 5,824,701 A | 10/1998 | Greenwald et al. |
| 5,869,680 A | 2/1999 | Mas et al. |
| 7,294,753 B2 | 11/2007 | Kloetzer et al. |
| 7,732,146 B2 | 6/2010 | Gaeta et al. |
| 7,799,824 B2 | 9/2010 | Lagu et al. |
| 8,067,415 B2 | 11/2011 | Elder et al. |
| 2004/0071780 A1 | 4/2004 | Lillard et al. |
| 2006/0058289 A1 | 3/2006 | Van Lommen et al. |
| 2006/0069123 A1 | 3/2006 | Xia et al. |
| 2007/0037794 A1 | 2/2007 | Ungashe et al. |
| 2007/0197590 A1 | 8/2007 | Demong et al. |
| 2008/0102114 A1 | 5/2008 | Koritala et al. |
| 2012/0258176 A1 | 10/2012 | Sung et al. |
| 2014/0023692 A1 | 1/2014 | Du Toit et al. |
| 2014/0363514 A1 | 12/2014 | Koyakutty et al. |
| 2016/0038612 A1 | 2/2016 | Hoge et al. |

FOREIGN PATENT DOCUMENTS

| | | |
|---|---|---|
| EP | 0590267 | 4/1994 |
| WO | 93/10076 | 5/1993 |
| WO | 93/23555 | 11/1993 |

(Continued)

OTHER PUBLICATIONS

Erdogar et al., Int'l J. of Pharmaceutics 471 (2014) 1-9 (Year: 2014).*
International Search Report and Written Opinion issued by the International Searching Authority (ISA/US) in PCT Application No. PCT/US2019/027105 dated Jul. 1, 2019. 8 pages.
Akagi, Takami, et al. "Preparation and characterization of biodegradable nanoparticles based on poly (γ-glutamic acid) with L-phenylalanine as a protein carrier." Journal of Controlled Release 108.2-3 (2005): 226-236.
Adamson P, Wilde T, Dobrzynski E, et al., "Single ocular injection of a sustained-released anti-VEFG delivers 6 months pharmacokinetics and efficacy in a primate laser CNV mode," J Control Release, 244(Pt A):1-13, 2016.
Adelman, R. A., Zheng, Q. & Mayer, H. R. Persistent ocular hypertension following intravitreal bevacizumab and ranibizumab injections. Journal of Ocular Pharmacology and Therapeutics 26, 105-110 (2010).

(Continued)

*Primary Examiner* — Robert S Cabral
(74) *Attorney, Agent, or Firm* — Meunier Carlin & Curfman LLC

(57) ABSTRACT

In one aspect, the disclosure relates to relates to compositions, devices, and processes for drug delivery to an eye. The disclosed drug delivery compositions comprise a particle having a core component comprising a first polymer and a therapeutic agent, and a shell layer surrounding the core component comprising a second polymer. In a further aspect, the present disclosure relates to methods of treating an ophthalmological disease or disorder. This abstract is intended as a scanning tool for purposes of searching in the particular art and is not intended to be limiting of the present disclosure.

17 Claims, 9 Drawing Sheets

(56) References Cited

FOREIGN PATENT DOCUMENTS

| WO | 94/07876 | 4/1994 |
|---|---|---|
| WO | 94/07880 | 4/1994 |
| WO | 94/07881 | 4/1994 |
| WO | 94/07882 | 4/1994 |
| WO | 98/13059 | 4/1998 |
| WO | 98/22451 | 5/1998 |
| WO | 98/28288 | 7/1998 |
| WO | 98/58927 | 12/1998 |
| WO | 99/09021 | 2/1999 |
| WO | 99/18113 | 4/1999 |
| WO | 2003/104203 | 12/2003 |
| WO | 2007/070961 | 6/2007 |
| WO | 2009/117706 | 9/2009 |
| WO | 2011053803 A2 | 5/2011 |
| WO | 2013126799 A1 | 8/2013 |

OTHER PUBLICATIONS

Akagawa K, Tsukada Y, "Presence and characteristics of catecholamine-sensitive Na—K-ATPase in rat stiatum," J Neurochem, 32:269-71, 1979.

Alm, Albert, and Anders Bill. "The oxygen supply to the retina, I. Effects of changes in intraocular and arterial blood pressures, and in arterial PO2 and PCO2 on the oxygen tension in the vitreous body of the cat." Acta physiologica Scandinavica 84.2 (1972): 261-274.

Alovisi C et al, "Vitreous substitutes: Old and new materials in vitreoretinal surgery," J Ophthalmol, 3172138, 2017.

Alves da Silva, M L et al. Cartilage tissue engineering using electrospun PCL nanofiber meshes and MSCs. Biomacromolecules 11, 3228-3236 (2010).

Andrew, J. S. et al. Sustained release of a monoclonal antibody from electrochemically prepared mesoporous silicon oxide. Advanced functional materials 20, 4168-4174 (2010).

Asasutjarit, R. et al. Development and evaluation of diclofenac sodium loaded-N-Trimethyl chitosan nanoparticles for ophthalmic use. Aaps Pharmscitech 16, 1013-1024 (2015).

Bai, Fengwei, et al. "A novel allosteric inhibitor of macrophage migration inhibitory factor (MIF)." Journal of Biological Chemistry 287.36 (2012): 30653-30663.

Barbault-Foucher, S., Gref, R., Russo, P., Guechot, J. & Bochot, A. Design of poly-ε-caprolactone nanospheres coated with bioadhesive hyaluronic acid for ocular delivery. J. Controlled Release 83, 365-375 (2002).

Beatty, S., Koh, H., Phil, M., Henson, D. & Boulton, M. The role of oxidative stress in the pathogenesis of age-related macular degeneration. Surv. Ophthalmol. 45, 115-134 (2000).

Beers RF, Sizer IW, "A spectrophotometric method for measuring the breakdown of hydrogen peroxide by catalase," J Biol Chem, 195:133-40, 1952.

Bennett LL, "Conventional and advanced ocular formulation and delivery: a mini review," J Clinical Medi Res Updates, 4:5-15, 2017.

Bernards, D. A. et al. Ocular biocompatibility and structural integrity of micro-and nano structured poly (caprolactone) films. Journal of Ocular Pharmacology and Therapeutics 29, 249-257 (2013).

Bhattarai, N., Edmondson, D., Veiseh, O., Matsen, F. A. & Zhang, M. Electrospun chitosan-based nanofibers and their cellular compatibility. Biomaterials 26, 6176-6184 (2005).

Bhise, Nupura S., et al. "Drug delivery strategies for therapeutic angiogenesis and antiangiogenesis." Expert opinion on drug delivery 8.4 (2011): 485-504.

Bhutto, I. A. et al. Pigment epithelium-derived factor (PEDF) and vascular endothelial growth factor (VEGF) in aged human choroid and eyes with age-related macular degeneration. Exp. Eye Res. 82, 99-110 (2006).

Bianchi, et al. (Mar. 1995). Molecular Medicine (Cambridge, Mass.) 1 (3): 254-266.

Bisht R, Abhirup M, Jaiswal JK, Rupenthal ID, "Nanocarrier mediated retinal drug delivery: overcoming ocular barriers to treat posterior eye diseases," WIREs Nanomed Nanobiotechnol, e1473, doi:10.1002/wnan.1473, 2017.

Bouchemal, K., Briançon, S., Perrier, E. & Fessi, H. Nano-emulsion formulation using spontaneous emulsification: solvent, oil and surfactant optimisation. International Journal of Pharmaceutics 280, 241-251 (2004).

Cao, Y. et al. Poly (N-isopropylacrylamide)-chitosan as thermosensitive in situ gel-forming system for ocular drug delivery. J. Controlled Release 120, 186-194 (2007).

Carrasquillo KG, Ricker JA, Rigas IK, et al., "Controlled delivery of the anti-VEGF aptamer EYE001 with poly(lactic-co-glycolic)acid microspheres," Invest Ophthalmol Vis Sci, 44(1):290-299, 2003.

Chandler HL et al, "Prevention of posterior capsular opacification through cyclooxygenase-2 inhibition," Mol Vis, 13:677-91, 2007.

Chang S, "LXII Edward Jackson lecture: Open-angle glaucoma after vitrectomy," Am J Ophthalmol, 141:1033-43, 2006.

Chen, M., Muckersie, E., Forrester, J. V. & Xu, H. Immune activation in retinal aging: a gene expression study. Invest. Ophthalmol. Vis. Sci. 51, 5888-5896 (2010).

Chirila TV et al, "Synthetic polymers as materials for artificial vitreous body review and recent advances," J Biomater Appl, 9:121-37, 1994.

Cipitria, A., et al. "Design, fabrication and characterization of PCL electrospun scaffolds—a review." Journal of Materials Chemistry 21.26 (2011): 9419-9453.

Comunian TA et al, "Microencapsulation of ascorbic acid by complex coacervation protection and controlled release," Food Res Int, 52(1):373-9, 2013.

Courtois, Fabienne, et al. "Rational design of therapeutic mAbs against aggregation through protein engineering and incorporation of glycosylation motifs applied to bevacizumab." MAbs. vol. 8. No. 1. Taylor & Francis, 2016.

Cunha-Vaz, J., Bernardes, R. & Lobo, C. Blood-retinal barrier. Eur. J. Ophthalmol. 21, 3-9 (2011).

Dash, T. K. & Konkimalla, V. B. Poly-ε-caprolactone based formulations for drug delivery and tissue engineering: A review. J. Controlled Release 158, 15-33 (2012).

Davis JL et al, "Liposomal-encapsulated ascorbic acid: influence on vitamin C bioavailability and capacity to protect against ischemia-reperfusion injury," Nutr Metab Insights, 9:25-30, 2016.

De la Fuente, M. et al. Chitosan-based nanostructures: a delivery platform for ocular therapeutics. Adv. Drug Deliv. Rev. 62, 100-117 (2010).

De Vrieze, S. et al. The effect of temperature and humidity on electrospinning. J. Mater. Sci. 44, 1357 (2009).

Del Amo EM, Rimpela AK, Heikkinen E, et al., "Pharmacokinetic aspects of retinal drug delivery," Prog Retin Eye Res, 57:134-185, 2017.

Del Amo EM, Urtti A, "Rabbit as an animal model for intravitreal pharmacokinetics: Clinical predictability and quality of the published data," Exp Eye Res, 137:111-24, 2015.

Dixon JA, Oliver SCN, Olson JL, Mandava N, "VEGF Trap-Eye for the treatment of neovascular age-related macular degeneration," Expert Opin Investig Drugs, 18(10):1573-1580, 2009.

Du JD, Fong W-K, Caliph S, Boyd BJ, "Lipid-based drug delivery systems in the treatment of wet age-related macular degeneration," Drug Deliv Transl Res, 6:781-792, 2016.

Dubey, R. R. & Parikh, R. H. Two-stage optimization process for formulation of chitosan microspheres. AAPS PharmSciTech 5, 20 (2004).

Ehlers, J. P. et al. Utility of intraoperative optical coherence tomography during vitrectomy surgery for vitreomacular traction syndrome. Retina 34, 1341 (2014).

Elsaid, N., Jackson, T. L., Elsaid, Z., Alqathama, A. & Somavarapu, S. PLGA Microparticles entrapping chitosan-based nanoparticles for the ocular delivery of ranibizumab. Molecular pharmaceutics 13, 2923-2940 (2016).

Federman JL, Schubert HD, "Complications associated with the use of silicone oil in 150 eyes after retinavitreous surgery," Ophthalmology, 95(7):870-6, 1988.

Feeney-Burns, L., Hilderbrand, E. S. & Eldridge, S. Aging human RPE morphometric analysis of macular, equatorial, and peripheral cells. Invest. Ophthalmol. Vis. Sci. 25, 195-200 (1984).

(56) References Cited

OTHER PUBLICATIONS

Folk, James C., and Edwin M. Stone. "Ranibizumab therapy for neovascular age-related macular degeneration." New England Journal of Medicine 363.17 (2010): 1648-1655.
Fritsche, L., Igl, W., Bailey, J. et al. A large genome-wide association study of age-related macular degeneration highlights contributions of rare and common variants. Nat Genet 48, 134-143 (2016). https://doi.org/10.1038/ng.3448.
Galvin, O. et al. A sustained release formulation of novel quininib-hyaluronan microneedles inhibits angiogenesis and retinal vascular permeability in vivo. J. Controlled Release 233, 198-207 (2016).
Gan, L. et al. Hyaluronan-modified core-shell liponanoparticles targeting CD44-positive retinal pigment epithelium cells via intravitreal injection. Biomaterials 34, 5978-5987 (2013).
Gártner, J. "Electron-microscopic study on the fibrillar network and fibrocyte-collagen interactions in the vitreous cortex at the ora serrata of human eyes with special regard to the role of disintegrating cells." Experimental eye research 42.1 (1986): 21-33.
Gártner, J. "The fine structure of the vitreous base of the human eye and pathogenesis of pars planitis." American Journal of Ophthalmology 71.6 (1971): 1317-1327.
Gass, J. D. M. Muller cell cone, an overlooked part of the anatomy of the fovea centralis: hypotheses concerning its role in the pathogenesis of macular hole and foveomacular retinoschisis. Arch. Ophthalmol. 117, 821-823 (1999).
Geng, X., Kwon, O. & Jang, J. Electrospinning of chitosan dissolved in concentrated acetic acid solution. Biomaterials 26, 5427-5432 (2005).
George, M. & Abraham, T. E. Polyionic hydrocolloids for the intestinal delivery of protein drugs: alginate and chitosan—a review. J. Controlled Release 114, 1-14 (2006).
Guélat, Bertrand, et al. "Model-based prediction of monoclonal antibody retention in ion-exchange chromatography." Journal of Chromatography A 1298 (2013): 17-25.
Hackett RB, McDonald TO. Ophthalmic toxicology and assessing ocular irritation. In: Marzulli FN, Maibach HI, editors. Dermatotoxicology. 5. Washington, DC: Hemisphere Publishing Corp; 1996. pp. 749-815.
Haghjou, N., Soheilian, M. & Abdekhodaie, M. J. Sustained release intraocular drug delivery devices for treatment of uveitis. Journal of ophthalmic & vision research 6, 317 (2011).
Haller, Julia A., et al. "Randomized, sham-controlled trial of dexamethasone intravitreal implant in patients with macular edema due to retinal vein occlusion." Ophthalmology 117.6 (2010): 1134-1146.
Harding JJ, "Free and protein-bound glutathione in normal and cataractous lenses," Biochem J, 117:957-60, 1979.
Hirani A, Grover A, Lee YW, Pathak Y, Sutariya V, "Triamcinolone acetonide nanoparticles incorporated in thermoreversible gels for age-related macular degeneration," Pharm Dev Technol, 21(1):61-67, 2016.
Holekamp NM, "The vitreous gel: more than meets the eye," Am J Ophthalmol, 149:32-6, 2010.
Huang, Z., Zhang, Y., Kotaki, M. & Ramakrishna, S. A review on polymer nanofibers by electrospinning and their applications in nanocomposites. Composites Sci. Technol. 63, 2223-2253 (2003).
Islam MS, Haque P, Rashid TU, et al., "Core-shell drug carrier from folate conjugated chitosan obtained from prawn shell for targeted doxorubicin delivery," J Mater Sci: Mater Med, 28:55, 2017.
Jaiswal, M., Kumar, M. & Pathak, K. Zero order delivery of itraconazole via polymeric micelles incorporated in situ ocular gel for the management of fungal keratitis. Colloids and Surfaces B: Biointerfaces 130, 23-30 (2015).
Jarrett, P. K. et al. Tolerability of Intravitreal Hydrogel Depots for Anti-VEGF Sustained Release in a Rabbit Model. Invest. Ophthalmol. Vis. Sci. 56, 1496 (2015).
Jeffery, H., Davis, S. S. & O'hagan, D. T. The preparation and characterisation of poly (lactide-co-glycolide) microparticles. I: Oil-in-water emulsion solvent evaporation. Int. J. Pharm. 77, 169-175 (1991).

Kaiser PK, "Emerging therapies for neovascular age-related macular degeneration," Ophthalmology, 120:S11-S15, 2013.
Kaiser RS et al, "The microsurgical safety task force: Evolving guidelines for minimizing the risk of endophthalmitis associated with microincisional vitrectomy surgery," Retina, 30(4):692-9, 2010.
Kaji H, Nagai N, Nishizawa M, Abe T, "Drug delivery devices for retinal diseases," Adv Drug Deliv Rev, In Press.
Kamiya T, Zigler JS, "Long-term maintenance of monkey lenses in organ culture: A potential model system for the study of human cataractogenesis," Exp Eye Res, 63:425-31, 1996.
Kamchanajindanun J, Srisa-ard M, Baimark Y, "Genipin-cross-linked chitosan microspheres prepared by a water-in-oil emulsion solvent diffusion method for protein delivery," Carbohydr Polym, 85(3):674-680, 2011.
Kennedy, C. J., Rakoczy, P. E. & Constable, I. J. Lipofuscin of the retinal pigment epithelium: a review. Eye 9, 763 (1995).
Kim, S. H., Lutz, R. J., Wang, N. S. & Robinson, M. R. Transport barriers in transscleral drug delivery for retinal diseases. Ophthalmic Res. 39, 244-254 (2007).
Kingston, David GI, G. Samranayake, and C. A. Ivey. "The chemistry of taxol, a clinically useful anticancer agent." Journal of Natural Products 53.1 (1990): 1-12.
Klein R, Wang Q, Klein BE, et al., "The relationship of age-related maculopathy, cataract, and glaucoma to visual acuity," Invest Ophthalmol Vis Sci, 36:182-191, 1995.
Klein, Robert J., et al. "Complement factor H polymorphism in age-related macular degeneration." Science 308.5720 (2005): 385-389.
Kleinberg, T. T., Tzekov, R. T., Stein, L., Ravi, N. & Kaushal, S. Vitreous substitutes: a comprehensive review. Surv. Ophthalmol. 56, 300-323 (2011).
Ko, J. A., Park, H. J., Hwang, S. J., Park, J. B. & Lee, J. S. Preparation and characterization of chitosan microparticles intended for controlled drug delivery. Int. J. Pharm. 249, 165-174 (2002).
Koo, H. et al. The movement of self-assembled amphiphilic polymeric nanoparticles in the vitreous and retina after intravitreal injection. Biomaterials 33, 3485-3493 (2012).
Kothandan, Gugan, Changdev G. Gadhe, and Seung Joo Cho. "Structural insights from binding poses of CCR2 and CCR5 with clinically important antagonists: a combined in silico study." PloS one 7.3 (2012): e32864.
Krzystolik, M. G. et al. Prevention of experimental choroidal neovascularization with intravitreal anti-vascular endothelial growth factor antibody fragment. Arch. Ophthalmol. 120, 338-346 (2002).
Kumar, M. N. R. A review of chitin and chitosan applications. React Funct Polym 46, 1-27 (2000).
Kuno, N. & Fujii, S. Recent advances in ocular drug delivery systems. Polymers 3, 193-221 (2011).
Lance KD, Bernards DA, Caccio NA, et al., "In vivo and in vitro sustained release of ranibizumab from a nanoporous thin-film device," Drug Deliv Transl Res, 6:771-780, 2016.
Lee SS, Hughes P, Ross AD, Robinson MR, "Biodegradable implants for sustained drug release in the eye," Pharm Res, 27:2043-2053, 2010.
Lee, J. Y., Chae, J. B., Yang, S. J., Yoon, Y. H. & Kim, J. Effects of intravitreal bevacizumab and laser in retinopathy of prematurity therapy on the development of peripheral retinal vessels. Graefe's Archive for Clinical and Experimental Ophthalmology 248, 1257-1262 (2010).
Lee, Jeongwoo, et al. "Controlling morphology of polymer microspheres by Shirasu porous glass (SPG) membrane emulsification and subsequent polymerization: from solid to hollow." Macromolecular research 18.12 (2010): 1142-1147.
Li, Qiutang, et al. "IKK2 inhibition using TPCA-1/PLGA microspheres attenuates the laser induced choroidal neovascularization." Investigative Ophthalmology & Visual Science 54.15 (2013): 2179-2179.
Li, F., Hurley, B., Liu, Y., Leonard, B. & Griffith, M. Controlled release of bevacizumab through nanospheres for extended treatment of age-related macular degeneration. The open ophthalmology journal 6, 54 (2012).
Li, S. Kevin, Mark R. Liddell, and He Wen. "Effective electrophoretic mobilities and charges of anti-VEGF proteins determined by

(56) References Cited

OTHER PUBLICATIONS capillary zone electrophoresis." Journal of pharmaceutical and biomedical analysis 55.3 (2011): 603-607.
Li, X. et al. Diclofenac/biodegradable polymer micelles for ocular applications. Nanoscale 4, 4667-4673 (2012).
Lidich, N., Wachtel, E. J., Aserin, A. & Garti, N. Water-dilutable microemulsions for transepithelial ocular delivery of riboflavin phosphate. J. Colloid Interface Sci. 463, 342-348 (2016).
Lim JC et al, "Novel roles for the lens in preserving overall ocular health," Exp Eye Res, 156:117-23, 2017.
Lim, L. S., Mitchell, P., Seddon, J. M., Holz, F. G. & Wong, T. Y. Age-related macular degeneration. The Lancet 379, 1728-1738 (2012).
Lindstrom R, "Thoughts on cataract surgery," Rev Ophthalmol, 2015.
Linetsky MD et al, "Glucose-derived Amadori compounds of glutathione," Biochim Biophys Acta, 1724:181-93, 2005.
Los LI et al., "Age-related liquefaction of the human vitreous body: LM and TEM evaluation of the role of proteoglycans and collagen," Invest Ophthalmol Vis Sci, 44:2828-33, 2003.
Lu, Y. et al. Effect of intravitreal injection of bevacizumab-chitosan nanoparticles on retina of diabetic rats. International journal of ophthalmology 7, 1 (2014).
Luo, Z. et al. Thermosensitive PEG-PCL-PEG (PECE) hydrogel as an in situ gelling system for ocular drug delivery of diclofenac sodium. Drug Deliv. 23, 63-68 (2016).
Lutty, G. A. et al. Development of the human choriocapillaris. Eye 24, 408 (2010).
Manchanda S, Sahoo PK, Majumdar DK, "Mucoadhesive chitosan-dextran sulfate nanoparticles of acetazolamide for ocular hypertension," Nanotechnol Rev, 5(5):445-453, 2016.
Manna S, Augsburger JJ, Correa ZM, et al., "Noninvasive electroretinography assessment of intravitreal sustained-release methotrexate microimplants in rabbit eyes," J Ocul Pharm Ther, 32(9):583-594, 2016.
Manna, S. et al. Biodegradable chitosan and polylactic acid-based intraocular microimplant for sustained release of methotrexate into vitreous: analysis of pharmacokinetics and toxicity in rabbit eyes. Graefe's Archive for Clinical and Experimental Ophthalmology 253, 1297-1305 (2015).
Marmor, M. F. & Wolfensberger, T. J. The retinal pigment epithelium. Function and disease.New York: Oxford, 103-134 (1998).
Maurice D, "Review: practical issues in intravitreal drug delivery," J Ocul Pharmacol Ther, 17:393-401, 2001.
May JM et al., "Reduction of dehydroascorbate to ascorbate by the selenoenzyme thioredoxin reductase," J Biol Chem, 272:22607-10, 1997.
Mi, F., Shyu, S., Chen, C. & Schoung, J. Porous chitosan microsphere for controlling the antigen release of Newcastle disease vaccine: preparation of antigen-adsorbed microsphere and in vitro release. Biomaterials 20, 1603-1612 (1999).
Min, B. et al. Chitin and chitosan nanofibers: electrospinning of chitin and deacetylation of chitin nanofibers. Polymer 45, 7137-7142 (2004).
Miquel, J., Economos, A. C., Fleming, J. & Johnson Jr, J. E. Mitochondrial role in cell aging. Exp. Gerontol. 15, 575-591 (1980).
Moraru, A. D. et al. Intraocular biodistribution of intravitreal injected chitosan/gelatin nanoparticles. Rom. J. Morphol. Embryol. 55, 869-875 (2014).
Munj, Hrishikesh R., John J. Lannutti, and David L. Tomasko. "Understanding drug release from PCL/gelatin electrospun blends." Journal of biomaterials applications 31.6 (2017): 933-949.
Murali, Karthik, et al. "Spatial variations in vitreous oxygen consumption." Plos one 11.3 (2016): e0149961.
Noh, H. K. et al. Electrospinning of chitin nanofibers: Degradation behavior and cellular response to normal human keratinocytes and fibroblasts. Biomaterials 27, 3934-3944 (2006).
O'Toole MG, Henderson RM, Soucy PA, et al., "Curcumin encapsulation in submicrometer spray-dried chitosan/tween 20 particles," Biomacromolecules, 13:2309-2314, 2012.

O'Toole MG, Soucy PA, Chauhan R, et al., "Release-modulated antioxidant activity of a composite curcumin-chitosan polymer," Biomacromolecules, 17:1253-1260, 2016.
Ohkawa, K., Cha, D., Kim, H., Nishida, A. & Yamamoto, H. Electrospinning of chitosan. Macromolecular Rapid Communications 25, 1600-1605 (2004).
Ohr M, Kaiser PK, "Intravitreal aflibercept injection for neovascular (wet) age-related macular degeneration," Expert Opin Pharmacotherapy, 13(4):585-591, 2012.
Okamura M, "An improved method for determination of L-ascorbic acid and L-dehydroascorbic acid in blood plasma," Clin Chim Acta, 103:259-68, 1980.
Omri, S. et al. The outer limiting membrane (OLM) revisited: clinical implications. Clinical ophthalmology (Auckland, NZ) 4, 183-195 (2010).
Paik, P. & Zhang, Y. Synthesis of hollow and mesoporous polycaprolactone nanocapsules. Nanoscale 3, 2215-2219 (2011).
Pal, R. A novel method to correlate emulsion viscosity data. Colloids and Surfaces A: Physicochemical and Engineering Aspects 137, 275-286 (1998).
Paris R, Quijada-Garrido I, "Swelling behaviour of thermo-sensitive hydrogels based on oligo(ethylene glycol) methacrylates," Eur Polym J, 45:3418-25, 2009.
Peng Y, Ang M, Foo S, et al., "Biocompatibility and biodegradation studies of subconjunctival implants in rabbit eyes," PLoS ONE, 6(7):e22507, 2011.
Prosperi-Porta, G., Muirhead, B. & Sheardown, H. Tunable release of ophthalmic therapeutics from injectable, resorbable, thermoresponsive copolymer scaffolds. Journal of Biomedical Materials Research Part B: Applied Biomaterials 105, 53-62 (2017).
Quigley HA, Broman AT, "The number of people with glaucoma worldwide in 2010 and 2020," Br J Ophthalmol, 90(3):262-7, 2006.
Radhakrishnan, K. et al. Protein delivery to the back of the eye: barriers, carriers and stability of anti-VEGF proteins. Drug Discov. Today 22, 416-423 (2017).
Rao MVL et al., "Inhibition of oxidation of ascorbic acid by EDTA," J Sci Food Agricul, 10(8):436-41, 1959.
Refojo MF, "Polymers in ophthalmic surgery," J Biomed Mater Res, 5:113-9, 1971.
Resnikoff, Serge, et al. "Global data on visual impairment in the year 2002." Bulletin of the world health organization 82 (2004): 844-851.
Ribo Peng, G. Q., Li, X., Lv, H., Qian, Z. & Yu, L. The PEG-PCL-PEG hydrogel as an implanted ophthalmic delivery system after glaucoma filtration surgery; a pilot study. Medical Hypothesis, Discovery and Innovation in Ophthalmology 3, 3 (2014).
Rizzo, J. F. Embryology, anatomy, and physiology of the afferent visual pathway. Clinical Neuro-Ophthalmology, 3-82 (2005).
Rizzo, S. et al. Injection of intravitreal bevacizumab (Avastin) as a preoperative adjunct before vitrectomy surgery in the treatment of severe proliferative diabetic retinopathy (PDR). Graefe's Archive for Clinical and Experimental Ophthalmology 246, 837-842 (2008).
Sahil, K., Akanksha, M., Premjeet, S., Bilandi, A. & Kapoor, B. Microsphere: a review. Int.J.Res.Pharm.Chem 1, 1184-1198 (2011).
Sampat, K. M. & Garg, S. J. Complications of intravitreal injections. Curr. Opin. Ophthalmol. 21, 178-183 (2010).
Sangiovanni, J. P. et al. The relationship of dietary carotenoid and vitamin A, E, and C intake with age-related macular degeneration in a case-control study. Arch. Ophthalmol. 125, 1225-1232 (2007).
Sangsanoh, P. & Supaphol, P. Stability improvement of electrospun chitosan nanofibrous membranes in neutral or weak basic aqueous solutions. Biomacromolecules 7, 2710-2714 (2006).
Schmitt, C. J., Lotti, V. J. & LeDouarec, J. C. Penetration of timolol into the rabbit eye: measurements after ocular instillation and intravenous injection. Arch. Ophthalmol. 98, 547-551 (1980).
Schnichels S et al, "Efficacy of two different thiol-modified cross-linked hyaluronate formulations as vitreous replacement compared to silicone oil in a model of retinal detachment," PLoS ONE, 12(3):e0172895, 2017.
Schubert, H. D. Ch 99-Structure and function of the neural retina. in Ophthalmology, 2010.

(56) References Cited

OTHER PUBLICATIONS

Seddon, J. M. et al. Dietary carotenoids, vitamins A, C, and E, and advanced age-related macular degeneration. JAMA 272, 1413-1420 (1994).
Sen HN et al, "A standardized grading system for scleritis," Ophthalmology, 118(4):768-71, 2011.
Shah MA et al, "Frequency of complications of silicone oil in the surgical treatment of rhegmatogenous retinal detachment," Pak J Ophthalmol, 33(2):74-8, 2017.
Shah, N. H., et al. "A biodegradable injectable implant for delivering micro and macromolecules using poly (lactic-co-glycolic) acid (PLGA) copolymers." Journal of Controlled Release 27.2 (1993): 139-147.
Shi, S. et al. Chitosan grafted methoxy poly (ethylene glycol)-poly (ε-caprolactone) nanosuspension for ocular delivery of hydrophobic diclofenac. Scientific reports 5, 11337 (2015).
Shui Y-B et al, "The gel state of the vitreous and ascorbate-dependent oxygen consumption: relationship to the etiology of nuclear cataracts," Arch Ophthalmol, 127:475-482, 2009.
Siegfried CJ et al, "Effects of vitrectomy and lensectomy on older rhesus macaques: Oxygen distribution, antioxidant status, and aqueous humor dynamics," Invest Ophthalmol Vis Sci, 58(10):4003-14, 2017.
Singh Malik, D., Mital, N. & Kaur, G. Topical drug delivery systems: a patent review. Expert opinion on therapeutic patents 26, 213-228 (2016).
Singh, S. R. et al. Intravenous transferrin, RGD peptide and dual-targeted nanoparticles enhance anti-VEGF intraceptor gene delivery to laser-induced CNV. Gene Ther. 16, 645 (2009).
Smith AG, Kaiser PK, "Emerging treatments for wet age-related macular degeneration," Expert Opin Emerg Drugs, 19(1):157-164, 2014.
Sonoda, S. et al. A protocol for the culture and differentiation of highly polarized human retinal pigment epithelial cells. Nature protocols 4, 662 (2009).
Spilsbury, K., Garrett, K. L., Shen, W., Constable, I. J. & Rakoczy, P. E. Overexpression of vascular endothelial growth factor (VEGF) in the retinal pigment epithelium leads to the development of choroidal neovascularization. The American journal of pathology 157, 135-144 (2000).
Sun, S. et al. Episcleral drug film for better-targeted ocular drug delivery and controlled release using multilayered poly-ε-caprolactone (PCL). Acta biomaterialia 37, 143-154 (2016).
Swindle KE et al, "In situ formation of hydrogels as vitreous substitutes: viscoelastic comparison to porcine vitreous," J Biomed Mater Res A, 87(3):656-65, 2008.
Swindle KE, Ravi N, "Recent advances in polymeric vitreous substitutes," Expert Rev Ophthalmol, 2(2):255-65, 2007.
Swindle-Reilly KE et al, "Current concepts in the design of hydrogels as vitreous substitutes," In Biomaterials and Regenerative Medicine in Ophthalmology, 2016.
Swindle-Reilly KE et al., "Rabbit study of an in situ forming hydrogel vitreous substitute," Invest Ophthalmol Vis Sci, 50(10):4840-6, 2009.
Szirmai, J. A. & Balazs, E. A. Studies on the structure of the vitreous body: III. Cells in the cortical layer. AMA archives of ophthalmology 59, 34-48 (1958).
Takano S et al, "Determination of ascorbic acid in human vitreous humor by high-performance liquid chromatography with UV detection," Curr Eye Res, 16(6):589-94, 1997.
Thrimawithana, T. R., Young, S., Bunt, C. R., Green, C. & Alany, R. G. Drug delivery to the posterior segment of the eye. Drug Discov. Today 16, 270-277 (2011).
Urtti, A. Challenges and obstacles of ocular pharmacokinetics and drug delivery. Adv. Drug Deliv. Rev. 58, 1131-1135 (2006).
Van Leeuwen, R. et al. Dietary intake of antioxidants and risk of age-related macular degeneration. JAMA 294, 3101-3107 (2005).
Varshosaz, J., Tabbakhian, M. & Salmani, Z. Designing of a thermosensitive chitosan/poloxamer in situ gel for ocular delivery of ciprofloxacin. The Open Drug Delivery Journal 2 (2008).
Villegas VM, Aranguren LA, Kovach JL, Schwartz SG, Flynn HW, "Current advances in the treatment of neovascular age-related macular degeneration," Expert Opin Drug Deliv, 14(2):273-282, 2017.
Wang, L., Ma, G. & Su, Z. Preparation of uniform sized chitosan microspheres by membrane emulsification technique and application as a carrier of protein drug. J. Controlled Release 106, 62-75 (2005).
Wang-Su ST et al, "Proteome analysis of lens epithelia, fibres, and the HLE B-3 cell line," Invest Ophthalmol Vis Sci, 44:4829-36, 2003.
Willoughby, C. E. et al. Anatomy and physiology of the human eye: effects of mucopolysaccharidoses disease on structure and function—a review. Clin. Experiment. Ophthalmol. 38, 2-11 (2010).
Wu, A. M. & Senter, P. D. Arming antibodies: prospects and challenges for immunoconjugates. Nat. Biotechnol. 23, 1137 (2005).
Wubben TJ et al, "Rates of vitrectomy among enrollees in a United States managed care network, 2001-2012," Ophthalmology, 123:590-8, 2016.
Xu, H., Chen, M. & Forrester, J. V. Para-inflammation in the aging retina. Prog. Retin. Eye Res. 28, 348-368 (2009).
Yin, H. et al. Toxicity evaluation of biodegradable and thermosensitive PEG-PCL-PEG hydrogel as a potential in situ sustained ophthalmic drug delivery system. Journal of Biomedical Materials Research Part B: Applied Biomaterials 92, 129-137 (2010).
Zhang J et al, "An injectable hydrogel prepared using a PEG/vitamin E copolymer facilitating aqueous driven gelation," 17(11):3648-58, 2016.
International Preliminary Report on Patentability issued for Application No. PCT/US2019/027105, dated Oct. 22, 2020.
Extended European Search Report issued for Application No. 19785098, dated Feb. 4, 2022.
Wu, Hua, et al. "Fabrication of core-shell microspheres using alginate and chitosan-polycaprolactone for controlled release of vascular endothelial growth factor." Reactive and Functional Polymers 72.7 (2012): 427-437.

* cited by examiner

METHODS AND COMPOSITIONS FOR SUSTAINED RELEASE MICROPARTICLES FOR OCULAR DRUG DELIVERY

CROSS-REFERENCE TO RELATED APPLICATIONS

This Application is a national stage application filed under 35 U.S.C. § 371 of PCT/US2019/027105, filed Apr. 11, 2019, which claims the benefit of U.S. Provisional Application No. 62/656,199, filed on Apr. 11, 2018, each of which is incorporated herein by reference in its entirety.

BACKGROUND

Age-related macular degeneration (AMD) is the fourth most common cause of blindness after cataracts, preterm birth, and glaucoma in the world. There are more than 11 million people diagnosed with wet AMD in the United States. It is estimated that this number will double in 30 years. Accordingly, much work has been done understanding disease pathogenesis and developing therapeutic methods. It is widely noted that overexpression of vascular endothelial growth factor (VEGF) along with aging stimulates neovascularization in the choroid, which leads to irreversible damages to the retina during bleeding and scarring of newly formed blood vessels. The current gold standard treatment for wet AMD is a monthly intravitreal injection of anti-VEGF such as bevacizumab or ranibizumab to inhibit VEGF and to prevent angiogenesis. However, frequent injections often lead to infection, elevated intraocular pressure and rhegmatogenous retinal detachment, as well as issues with patient compliance.

Recently, there have been reports of novel devices such as implant and micro/nanoparticles for a long-term drug delivery in the eye. Unfortunately, such implants require surgical procedures for implantation and removal. Moreover, the presently known implant devices tend to be off-target and lower the drug efficacy. Although microparticles or nanoparticles have a relatively small size appropriate for injection into the eye with 30 gauge needle, currently described microparticles or nanoparticles release therapeutic agents such as anti-VEGF therapeutics over a rapid window of release due to the biodegradation of known particle compositions in the first three months.

Accordingly, despite significant efforts directed to treatment of AMD, there remains a scarcity of methods and compositions that minimize deleterious side-effects of currently available treatment regiments. Moreover, there is a need for drug delivery systems and compositions that can be biodegradable and control the drug release up to six months after an intravitreal injection. There remains a need for an improved therapeutic approaches for the treatment of AMD and other ocular diseases requiring delivery of therapeutic agents to directly to the eye. These needs and other needs are satisfied by the present disclosure.

SUMMARY

In accordance with the purpose(s) of the present disclosure, as embodied and broadly described herein, the disclosure, in one aspect, relates to compositions, devices, and processes for drug delivery to an eye. The disclosed drug delivery compositions comprise a particle having a core component comprising a first polymer and a therapeutic agent, and a shell layer surrounding the core component comprising a second polymer. In a further aspect, the present disclosure relates to methods of treating an ophthalmological disease or disorder.

Disclosed are drug delivery compositions comprising particles having: a core component comprising a therapeutic agent and a first polymer having a net positive charge under physiological conditions; a shell layer comprising a second polymer that is biodegradable under physiological conditions.

Also disclosed are methods for treating an ophthalmological disorder, the method comprising injecting a therapeutically effective amount of a disclosed drug delivery composition into an eye of a subject.

Also disclosed are medicaments comprising a disclosed drug delivery composition.

Also disclosed are kits comprising a disclosed drug delivery composition, an article comprising a drug delivery composition, and/or instructions for administering a disclosed drug delivery composition.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figures 1A, 1B:
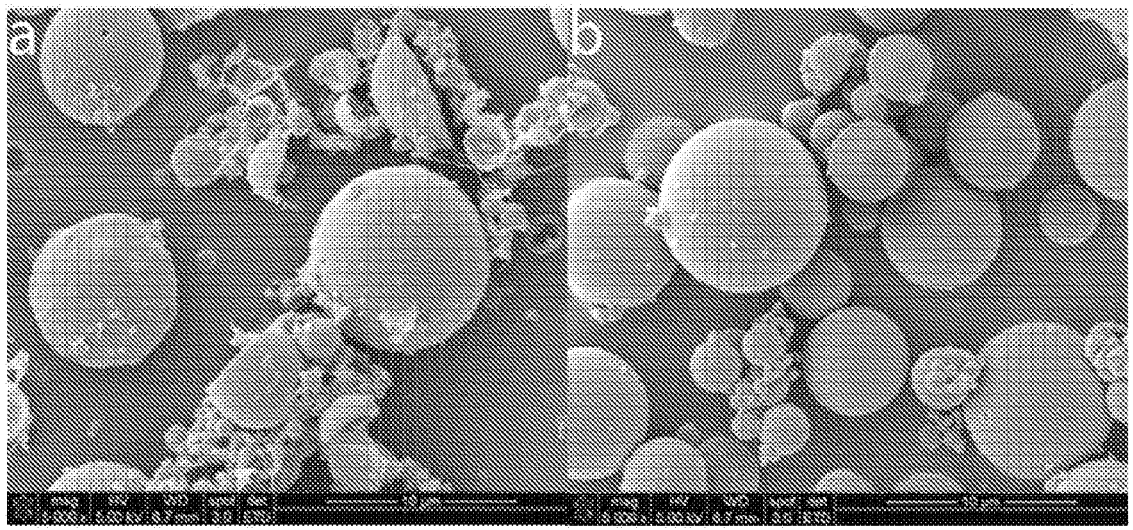
FIGS. 1A and 1B are SEM micrographs of chitosan MP prepared without SPG membrane under 600 rpm agitation at 0.5% (w/v) (FIG. 1A) and 1% (w/v) (FIG. 1B).

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Additionally, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a microparticle," "a polymer," or "a therapeutic agent," including, but not limited to, two or more such microparticles, polymers, or therapeutic agents, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "associated with" means mixed with, dispersed within, coupled to, covering, or surrounding.

As used herein, the terms "optional" or "optionally" means that the subsequently described event or circumstance can or cannot occur, and that the description includes instances where said event or circumstance occurs and instances where it does not.

As used herein, the terms "effective amount" and "amount effective" refer to an amount that is sufficient to achieve the desired result or to have an effect on an undesired condition, disorder, or disease. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

It is further understood that the term "therapeutically effective amount" as used in reference to the disclosed drug delivery compositions and methods refers to the level or amount of a disclosed composition comprising a therapeutic agent needed to treat a disclosed clinical condition, such as an ocular condition, or reduce or prevent ocular injury or damage, without causing significant negative or adverse side effects to the eye or a region of the eye, or treat a cancer with acceptable side effects to the patient.

The disclosed drug delivery compositions when used for intraocular administration have been developed which can release drug loads over various' time periods. These systems, which when placed into an eye of an individual, such as the vitreous of an eye, provide therapeutic levels of a macromolecule therapeutic agent for extended periods of time (e.g., for about one week or more). In certain aspects, the macromolecule therapeutic agent is a recombinant protein, purified protein, antibody, nucleic acid (such as a recombinant DNA, RNA, siRNA and the like) selected from the group consisting of anti-angiogenesis, ocular hemorrhage treatment, non-steroidal anti-inflammatory, growth factor (e.g. VEGF) inhibitor, growth factor, cytokines and antibiotics. The disclosed drug delivery compositions can be effective in treating ocular conditions, such as posterior ocular conditions, such as glaucoma and neovascularization, and generally improving or maintaining vision in an eye.

The term "treat", "treating", or "treatment" as used herein, refers to reduction or resolution or prevention of a disclosed clinical condition, such as an ocular condition, ocular injury or damage, or to promote healing of injured or damaged ocular tissue, or a cancer.

As used herein, a "therapeutic agent" refers to one or more therapeutic agents, active ingredients, or substances that can be used to treat a medical condition of the eye or a cancer. The therapeutic component is typically homogenously distributed throughout the disclosed drug delivery compositions. The therapeutic agents are typically ophthalmically acceptable, and are provided in a form that does not cause adverse reactions when the implant is placed in an eye. As discussed herein, the therapeutic agents can be released from the disclosed drug delivery compositions in a biologically active form. For example, the therapeutic agents may retain their three dimensional structure when released from the system into an eye.

It is further understood, that as used herein, the terms "therapeutic agent" includes any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, anti-arrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, an "intraocular drug delivery composition" refers to a composition that is structured, sized, or otherwise configured to be placed in an eye. The disclosed drug delivery compositions are generally biocompatible with physiological conditions of an eye and do not cause unacceptable or undesirable adverse side effects. The disclosed drug delivery compositions may be placed in an eye without disrupting vision of the eye. The present drug delivery system comprises a plurality of nanoparticles.

As used herein, an "ocular region" or "ocular site" refers generally to any area of the eyeball, including the anterior and posterior segment of the eye, and which generally includes, but is hot limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plane, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris; the posterior chamber (behind the iris, but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

As used herein, the term "cancer drugs" refers to conventional and well known chemical and biological (i.e, non-cellular) agents used to treat cancer and is sometimes referred to as "conventional therapy" or "conventional treatment". Such conventional therapy includes, but is not limited to, chemotherapy using anti-tumor chemicals, radiation therapy, hormonal therapy, and the like as well as combinations thereof. The term can also include antibodies and fragments thereof that are useful to treat or prevent cancer or tumors.

The term "biodegradable polymer" refers to a polymer or polymers which degrade in vivo, and wherein erosion of the polymer or polymers over time occurs concurrent with or subsequent to release of the therapeutic agent. The terms "biodegradable" and "bioerodible" are equivalent and are used interchangeably herein. A biodegradable polymer may be a homopolymer, a copolymer, or a polymer comprising more than two different polymeric units.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

Unless otherwise specified, temperatures referred to herein are based on atmospheric pressure (i.e. one atmosphere).

In various aspects, the present disclosure pertains to controlled release drug delivery systems comprising microparticles comprising the disclosed compositions. The disclosed controlled release drug delivery systems are capable of treating a variety of ocular diseases, and in various aspects, the disclosed drug delivery systems can be administered by intravitreal injection. The disclosed drug delivery systems can be used to treat retinal diseases, including glaucoma.

Drug Delivery Compositions

The disclosed drug delivery compositions comprise a chitosan core prepared as described herein below. It is understood that reference to a "chitosan core" is inclusive of a chitosan core without (or substantially free thereof) one or more therapeutic agents (e.g., useful as a control material) and a chitosan core comprising one or more therapeutic agents. The drug delivery compositions further comprise particles comprising a chitosan core with one or more therapeutic agents, further comprising a shell material encompassing in whole or in part, including substantially encompassing the chitosan core.

In various aspects, the disclosed drug delivery composition comprises particles having: a core component comprising a therapeutic agent and a first polymer having a net positive charge under physiological conditions; a shell layer comprising a second polymer that is biodegradable under physiological conditions.

In some aspects, the first polymer can comprise a chitosan, a polyethylenimine, a protamine, a polypropylenimine, a poly-L-lysine, a poly-L-arginine, a poly-D-lysine, a poly-D-arginine, derivatives thereof, and combinations thereof.

In some instances, the first polymer comprises a chitosan or derivative thereof. The chitosan in the disclosed drug delivery composition can have a degree of deacetylation of about 60% to about 90%; a degree of deacetylation of at least about 70%; a degree of deacetylation of at least about 75%; a degree of deacetylation of at least about 80%; or a range of degree of deacetylation encompassed by any for foregoing values; or any combination of the foregoing values.

In various aspects, the first polymer has a molecular weight of about 50,000 Da to about 500,000 Da; a molecular weight of about 100,000 Da to about 500,000 Da; a molecular weight of about 100,000 Da to about 400,000 Da; a molecular weight of about 200,000 Da to about 400,000 Da; a molecular weight of about 300,000 Da to about 400,000 Da; a molecular weight of about 310,000 Da to about 375,000 Da; a molecular weight sub-range within any of the foregoing ranges; or a molecular weight or combination of molecular weights within any of the foregoing ranges.

In some aspects, the second polymer comprises a poly (ε-caprolactone) (PCL), a poly-lactic acid (PLA), a poly-glycolic acid (PGA), a poly-lactide-co-glycolide (PLGA), a polyester, a poly (ortho ester), a poly(phosphazine), a poly (phosphate ester), a gelatin, a collagen, a polyethyleneglycol (PEG), derivatives thereof, and combinations thereof. In other aspects, the second polymer can be a suitable biocompatible polymer such as poly(lactide-co-glycolide) (PLGA), poly caprolactone (PCL), poly(lactic acid) (PLA), poly (glycolic acid) (PGA), polyethylene glycol, polysorbate, poly(ε-caprolactone-co-ethyl ethylene phosphate) (PCLEEP), polyvinyl alcohol (PVA), and combinations thereof. In certain aspects, the shell material comprises a biocompatible polymer selected from as poly(lactide-coglycolide) (PLGA), poly caprolactone (PCL), poly(lactic acid) (PLA), poly(glycolic acid) (PGA), and combinations thereof. In a further aspect, the shell material comprises a biocompatible polymer selected from poly(lactide-co-glycolide) (PLGA), poly caprolactone (PCL), poly(lactic acid) (PLA), and combinations thereof. In a still further aspect, the shell material comprises poly(lactide-co-glycolide) (PLGA). In a yet further aspect, the shell material comprises, poly caprolactone (PCL). In an even further aspect, the shell material comprises poly(lactic acid) (PLA).

In various aspects, the disclosed drug delivery composition comprises particles that are nanoparticles, microparticles, and combinations thereof. The particle size range for the disclosed drug delivery composition can be a size range of a size range of about 50 nm to about 1 μm; about 50 nm to about 100 μm; a size range of about 1 μm to about 50 μm; a size range of about 5 μm to about 20 μm; a size range of about 1 μm to about 15 μm; a size range of about 2 μm to about 15 μm; a size range of about 3 μm to about 15 μm; a size range of about 4 μm to about 15 μm; a size range of about 5 μm to about 15 μm; a size range of about 6 μm to about 15 μm; a size range of about 7 μm to about 15 μm; a size range of about 8 μm to about 15 μm; a size range of about 9 μm to about 15 μm; a size range of about 10 μm to about 15 μm; a size range of about 11 μm to about 15 μm; a size range of about 12 μm to about 15 μm; a size range of about 13 μm to about 15 μm; a size range of about 14 μm to about 15 μm; a size range of about 1 μm to about 16 μm; a size range of about 2 μm to about 16 μm; a size range of about 3 μm to about 16 μm; a size range of about 4 μm to about 16 μm; a size range of about 5 μm to about 16 μme; a size range of about 6 μm to about 16 μm; a size range of about 7 μm to about 16 μm; a size range of about 8 μm to about 16 μm; a size range of about 9 μm to about 16 μm; a size range of about 10 μm to about 16 μm; a size range of about 11 μm to about 16 μm; a size range of about 12 μm to about 16 μm; a size range of about 13 μm to about 16 μm; a size range of about 14 μm to about 16 μm; a size range of about 15 μm to about 16 μm; a size range of about 16 μm to about 16 μm; a size range of about 17 μm to about 16 μm; a size range of about 18 μm to about 16 μm; a size range of about 19 μm to about 16 μm; a size range of about 1 μm to about 17 μm; a size range of about 2 μm to about 17 μm; a size range of about 3 μm to about 17 μm; a size range of about 4 μm to about 17 μm; a size range of about 5 μm to about 17 μme; a size range of about 6 μm to about 17 μm; a size range of about 7 μm to about 17 μm; a size range of about 8 μm to about 17 μm; a size range of about 9 μm to about 17 μm; a size range of about 10 μm to about 17 μm; a size range of about 11 μm to about 17 μm; a size range of about 12 μm to about 17 μm; a size range of about 13 μm to about 17 μm; a size range of about 14 μm to about 17 μm; a size range of about 15 μm to about 17 μm; a size range of about 16 μm to about 17 μm; a size range of about 17 μm to about 17 μm; a size range of about 18 μm to about 17 μm; a size range of about 19 μm to about 17 μm; a size range of about 1 μm to about 18 μm; a size range of about 2 μm to about 18 μm; a size range of about 3 μm to about 18 μm; a size range of about 4 μm to about 18 μm; a size range of about 5 μm to about 18 μme; a size range of about 6 μm to about 18 μm; a size range of about 7 μm to about 18 μm; a size range of about 8 μm to about 18 μm; a size range of about 9 μm to about 18 μm; a size range of about 10 μm to about 18 μm; a size range of about 11 μm to about 18 μm; a size range of about 12 μm to about 18 μm; a size range of about 13 μm to about 18 μm; a size range of about 14 μm to about 18 μm; a size range of about 15 μm to about 18 μm; a size range of about 16 μm to about 18 μm; a size range of about 17 μm to about 18 μm; a size range of about 18 μm to about 18 μm; a size range of about 19 μm to about 18 μm; a size range of about 1 μm to about 19 μm; a size range of about 2 μm to about 19 μm; a size range of about 3 μm to about 19 μm; a size range of about 4 μm to about 19 μm; a size range of about 5 μm to about 19 μme; a size range of about 6 μm to about 19 μm; a size range of about 7 μm to about 19 μm; a size range of about 8 μm to about 19 μm; a size range of about 9 μm to about 19 μm; a size range of about 10 μm to about 19 μm; a size range of about 11 μm to about 19 μm; a size range of about 12 μm to about 19 μm; a size range of about 13 μm to about 19 μm; a size range of about 14 μm to about 19 μm; a size range of about 15 μm to about 19 μm; a size range of about 16 μm to about 19 μm; a size range of about 17 μm to about 19 μm; a size range of about 18 μm to about 19 μm; a size range of about 19 μm to about 19 μm; a size range of about 1 μm to about 20 μm; a size range of about 2 μm to about 20 μm; a size range of about 3 μm to about 20 μm; a size range of about 4 μm to about 20 μm; a size range of about 5 μm to about 20 μm; a size range of about 6 μm to about 20 μm; a size range of about 7 μm to about 20 μm; a size range of about 8 μm to about 20 μm; a size range of about 9 μm to about 20 μm; a size range of about 10 μm to about 20 μm; a size range of about 11 μm to about 20 μm; a size range of about 12 μm to about 20 μm; a size range of about 13 μm to about 20 μm; a size range of about 14 μm to about 20 μm; a size range of about 15 μm to about 20 μm; a size range of about 16 μm to about 20 μm; a size range of about 17 μm to about 20 μm; a size range of about 18 μm to about 20 μm; a size range of about 19 μm to about 20 μm; a size sub-range within any of the foregoing ranges; or a size or combination of sizes within any of the foregoing ranges.

In various aspects, the disclosed drug delivery composition comprises particles that are essentially spherical, spheroid, ellipsoid, or combinations thereof.

In some aspects, the disclosed drug delivery composition comprises particles with a size range of about 50 nm to about 100 μm and a shell layer with a thickness of about 10 nm to about 1 μm; particles with a size range of about 50 nm to about 100 μm and a shell layer with a thickness of about 10 nm to about 1 μm; particles with a size range of about 1 μm to about 50 μm and a shell layer with a thickness of about 10 nm to about 1 μm; particles with a size range of about 5 μm to about 20 μm and a shell layer with a thickness of about 10 nm to about 1 μm; particles have a size range of about 50 nm to about 1 μm and a shell layer with a thickness of about 10 nm to about 1 μm.

In various aspects, the disclosed drug delivery composition comprises particles with a shell layer having a thickness of about 100 nm to about 5 μm; about 200 nm to about 5 μm; about 300 nm to about 5 μm; about 400 nm to about 5 μm; about 500 nm to about 5 μm; about 600 nm to about 5 μm; about 700 nm to about 5 μm; about 800 nm to about 5 μm; about 900 nm to about 5 μm; about 1 μm to about 5 μm; about 1.1 μm to about 5 μm; about 1.2 μm to about 5 μm; about 1.3 μm to about 5 μm; about 1.4 μm to about 5 μm; about 1.5 μm to about 5 μm; about 1.5 μm to about 5 μm; about 1.6 μm to about 5 μm; about 1.7 μm to about 5 μm; about 1.8 μm to about 5 μm; about 1.9 μm to about 5 μm; about 2 μm to about 5 μm; about 1.1 μm to about 4 μm; about 1.2 μm to about 4 μm; about 1.3 μm to about 4 μm; about 1.4 μm to about 4 μm; about 1.5 μm to about 4 μm; about 1.5 μm to about 4 μm; about 1.6 μm to about 4 μm; about 1.7 μm to about 4 μm; about 1.8 μm to about 4 μm; about 1.9 μm to about 4 μm; about 2 μm to about 4 μm; about 1.1 μm to about 4.5 µm; about 1.2 µm to about 4.5 µm; about 1.3 µm to about 4.5 µm; about 1.4 µm to about 4.5 µm; about 1.5 µm to about 4.5 µm; about 1.5 µm to about 4.5 µm; about 1.6 µm to about 4.5 µm; about 1.7 µm to about 4.5 µm; about 1.8 µm to about 4.5 µm; about 1.9 µm to about 4.5 µm; about 2 µm to about 4.5 µm; about 1.1 µm to about 3 µm; about 1.2 µm to about 3 µm; about 1.3 µm to about 3 µm; about 1.4 µm to about 3 µm; about 1.5 µm to about 3 µm; about 1.5 µm to about 3 µm; about 1.6 µm to about 3 µm; about 1.7 µm to about 3 µm; about 1.8 µm to about 3 µm; about 1.9 µm to about 3 µm; about 2 µm to about 3 µm; about 1.1 µm to about 3.5 µm; about 1.2 µm to about 3.5 µm; about 1.3 µm to about 3.5 µm; about 1.4 µm to about 3.5 µm; about 1.5 µm to about 3.5 µm; about 1.5 µm to about 3.5 µm; about 1.6 µm to about 3.5 µm; about 1.7 µm to about 3.5 µm; about 1.8 µm to about 3.5 µm; about 1.9 µm to about 3.5 µm; about 2 µm to about 3.5 µm; about 1.1 µm to about 2 µm; about 1.2 µm to about 2 µm; about 1.3 µm to about 2 µm; about 1.4 µm to about 2 µm; about 1.5 µm to about 2 µm; about 1.5 µm to about 2 µm; about 1.6 µm to about 2 µm; about 1.7 µm to about 2 µm; about 1.8 µm to about 2 µm; about 1.9 µm to about 2 µm; about 1.1 µm to about 2.5 µm; about 1.2 µm to about 2.5 µm; about 1.3 µm to about 2.5 µm; about 1.4 µm to about 2.5 µm; about 1.5 µm to about 2.5 µm; about 1.5 µm to about 2.5 µm; about 1.6 µm to about 2.5 µm; about 1.7 µm to about 2.5 µm; about 1.8 µm to about 2.5 µm; about 1.9 µm to about 2.5 µm; about 2 µm to about 2.5 µm; a shell layer range that is a sub-range of any of the foregoing ranges; or a shell layer thickness that is a value within any of the foregoing ranges.

In various aspects, the disclosed drug delivery composition has a shell layer that comprises about 0.1 wt % to about 25 wt % based on the total weight of the first polymer and the second polymer; about 0.1 wt % to about 10 wt % based on the total weight of the first polymer and the second polymer; about 0.1 wt % to about 5 wt % based on the total weight of the first polymer and the second polymer; about 75 wt % to about 99.9 wt % based on the total weight of the first polymer and the second polymer; about 90 wt % to about 99.9 wt % based on the total weight of the first polymer and the second polymer; about 95 wt % to about 99.9 wt % based on the total weight of the first polymer and the second polymer.

In various aspects, the therapeutic agent is present in the disclosed drug delivery composition in an amount of about 0.1 wt % to about 75 wt % based on the total weigh of the first polymer, the second polymer, and the therapeutic agent; about 30 wt % to about 60 wt % based on the total weigh of the first polymer, the second polymer, and the therapeutic agent; about 45 wt % to about 55 wt % based on the total weigh of the first polymer, the second polymer, and the therapeutic agent.

In some aspects, the therapeutic agent is present in the disclosed drug delivery composition in an amount (in µg therapeutic agent per mg of the disclosed drug delivery composition) of about 10, about 20, about 30, about 35, about 40, about 45, about 50, about 55, about 60, about 65, about 70, about 75, about 80, about 85, about 90, about 95, about 100, about 110, about 120, about 130, about 135, about 140, about 145, about 150, about 155, about 160, about 165, about 170, about 175, about 180, about 185, about 190, about 195, about 200, about 210, about 220, about 230, about 235, about 240, about 245, about 250, about 255, about 260, about 265, about 270, about 275, about 280, about 285, about 290, about 295, about 300, about 310, about 320, about 330, about 335, about 340, about 345, about 350, about 355, about 360, about 365, about 370, about 375, about 380, about 385, about 390, about 395, about 400, about 410, about 420, about 430, about 435, about 440, about 445, about 450, about 455, about 460, about 465, about 470, about 475, about 480, about 485, about 490, about 495, about 500; or an amount range of the therapeutic agent (in µg therapeutic agent per mg of the disclosed drug delivery composition) bracketed by any two of the foregoing values; or any combination of the foregoing values.

In various aspects, the disclosed drug delivery compositions have a surface charge measured as a zeta potential at pH 7.4 has a value of about −25 mV to about 25 mV; about −20 mV to about 20 mV; about −15 mV to about 15 mV; about −10 mV to about 10 mV; about −7.5 mV to about 7.5 mV; about −5 mV to about 5 mV; about −4 mV to about 4 mV; about −3 mV to about 3 mV; about −2 mV to about 2 mV; about −1 mV to about 1 mV; about −0.5 mV to about 0.5 mV; a zeta potential range that is a sub-range of any of the foregoing ranges; or any zeta potential value or combination of values within the foregoing ranges.

In various aspects, the disclosed drug delivery compositions release an amount of drug (percent release based on the amount of drug initially present) after 30 days in phosphate-buffered saline at pH 7.4 of about 1% to about 75; about 5% to about 50%; about 5% to about 40%; about 5% to about 30%; about 5% to about 20%; about 5% to about 10%; a range of release that is a sub-range within any of the foregoing ranges; or a percent release or combination of percent release values that is within any of the foregoing ranges.

In various aspects, the disclosed drug delivery compositions release have a $t_{1/2}$ for amount of drug released (based on the amount of drug initially present and release kinetics for release after 30 days in phosphate-buffered saline at pH 7.4) of about 3 months to about 12 months; about 3 months to about 9 months; about 3 months to about 6 months; about 6 months to about 9 months; about 6 months to about 12 months; of at least about 1 month; of at least about 3 months; of at least about 6 months; of at least about 9 months; a $t_{1/2}$ for amount of drug released sub-range within any of the foregoing ranges; or a value or combination of values for $t_{1/2}$ for amount of drug released that is within any of the foregoing ranges.

In various aspects, the therapeutic agent has a net negative charge at pH 7.4.

A variety of therapeutic agents can be used with the disclosed drug delivery compositions, including therapeutic agents useful for treating an eye disease or a cancer. In some aspects, the disclosed drug delivery compositions comprise an anti-VEGF therapeutic agent, such as, but not limited to, bevacizumab, ranibizumab, lapatinib, sunitinib, sorafenib, axitinib, pazopanib, pharmaceutically acceptable salts thereof, and combinations thereof. In particular aspects, the disclosed drug delivery compositions comprise bevacizumab, ranibizumab, pharmaceutically acceptable salts thereof, and combinations thereof. In a further aspect, the disclosed drug delivery compositions comprise bevacizumab. In a still further aspect, the disclosed drug delivery compositions comprise is ranibizumab. In some aspects, the anti-VEGF therapeutic can be selected from lapatinib, sunitinib, sorafenib, axitinib, pazopanib, pharmaceutically acceptable salts thereof, and combinations thereof.

In various aspects, the shell material can be a suitable biocompatible polymer such as poly(lactide-co-glycolide) (PLGA), poly caprolactone (PCL), poly(lactic acid) (PLA), poly(glycolic acid) (PGA), polyethylene glycol, polysorbate, poly(ε-caprolactone-co-ethyl ethylene phosphate) (PCLEEP), polyvinyl alcohol (PVA), and combinations thereof. In certain aspects, the shell material comprises a biocompatible polymer selected from as poly(lactide-co-glycolide) (PLGA), poly caprolactone (PCL), poly(lactic acid) (PLA), poly(glycolic acid) (PGA), and combinations thereof. In a further aspect, the shell material comprises a biocompatible polymer selected from poly(lactide-co-glycolide) (PLGA), poly caprolactone (PCL), poly(lactic acid) (PLA), and combinations thereof. In a still further aspect, the shell material comprises poly(lactide-co-glycolide) (PLGA). In a yet further aspect, the shell material comprises, poly caprolactone (PCL). In an even further aspect, the shell material comprises poly(lactic acid) (PLA).

In some aspects, the disclosed drug delivery compositions are of a particle size such that such that they can be injected via 31-gauge needle. Accordingly, in such instances, the microparticle size should less than about 30 µm in diameter. However, if the disclosed drug delivery compositions are too small, the drug loading capacity will decrease to a clinically less useful amount. Accordingly, the size range of disclosed drug delivery composition for injection via a 31-gauge needle can be from about 10 µm to about 30 µm in diameter. In such instances, it may be useful to have a shell material, such as PCL, with a thickness of about 1-2 µm. In some aspects, the disclosed drug delivery compositions have a core wt % range in the core-shell particle when disclosed drug delivery compositions have a size range of about 10 µm to about 20 µm in diameter of about 70 wt % to about 75 wt %, about 65 wt % to about 75 wt %, about 60 wt % to about 75 wt %, about 55 wt % to about 75 wt %, about 50 wt % to about 75 wt %, about 45 wt % to about 75 wt %, about 40 wt % to about 75 wt %, about 35 wt % to about 75 wt %, about 30 wt % to about 75 wt %, about 25 wt % to about 75 wt %, about 20 wt % to about 75 wt %, about 65 wt % to about 70 wt %, about 60 wt % to about 70 wt %, about 55 wt % to about 70 wt %, about 50 wt % to about 70 wt %, about 45 wt % to about 70 wt %, about 40 wt % to about 70 wt %, about 35 wt % to about 70 wt %, about 30 wt % to about 70 wt %, about 25 wt % to about 70 wt %, about 20 wt % to about 70 wt %, 60 wt % to about 65 wt %, about 55 wt % to about 65 wt %, about 50 wt % to about 65 wt %, about 45 wt % to about 65 wt %, about 40 wt % to about 65 wt %, about 35 wt % to about 65 wt %, about 30 wt % to about 65 wt %, about 25 wt % to about 65 wt %, about 20 wt % to about 65 wt %, about 55 wt % to about 60 wt %, about 50 wt % to about 60 wt %, about 45 wt % to about 60 wt %, about 40 wt % to about 60 wt %, about 35 wt % to about 60 wt %, about 30 wt % to about 60 wt %, about 25 wt % to about 60 wt %, about 20 wt % to about 60 wt %, about 50 wt % to about 55 wt %, about 45 wt % to about 55 wt %, about 40 wt % to about 55 wt %, about 35 wt % to about 55 wt %, about 30 wt % to about 55 wt %, about 25 wt % to about 55 wt %, about 20 wt % to about 55 wt %, about 45 wt % to about 50 wt %, about 40 wt % to about 50 wt %, about 35 wt % to about 50 wt %, about 30 wt % to about 50 wt %, about 25 wt % to about 50 wt %, about 20 wt % to about 50 wt %; or a wt % sub-range within any of the foregoing ranges; or a wt % value or combination of values within any of the foregoing ranges.

Methods of Preparing a Disclosed Drug Delivery Composition

In various aspects, the disclosed drug delivery compositions are prepared by the methods disclosed herein below and as described in specific aspects in the representative Examples that follow. In general, the methods comprise a sequential process comprising preparation of chitosan core particles, followed by coating the chitosan core particles with a shell material.

In some aspects, the chitosan core particles can be prepared using a water-in-oil emulsion. The method of preparing the chitosan core particles can comprise using a solution of comprising chitosan and one or more therapeutic agents in a suitable solvent or buffer solution. The aqueous solution comprising the chitosan and the one or more therapeutic agents in a suitable solvent or buffer solution can then be dispersed into an oil phase. In some instances, the oil phase further comprises one or more surfactants. The aqueous solution comprising the chitosan and the one or more therapeutic agents in a suitable solvent or buffer solution can then be dispersed into the oil phase in a suitable volume ratio, and homogenized in the oil phase following dispersion. In some aspects, following homogenization, a cross-linking agent can be added thereto, e.g., a cross-linking agent capable of cross-linking the amino groups in the chitosan. The cross-linking agent can be added slowly over a suitable period of time at a suitable molar ratio of cross-linking groups to amino groups in the chitosan. Following cross-linking, the chitosan core particles can be isolated by any suitable method, e.g., centrifugation. Following centrifugation, the chitosan core particles are washed with one or more solvents one or more times. For example, the chitosan core particles can be washed sequentially with solvents such as petroleum ether, then acetone. For storage, the washed chitosan core particles can be freeze dried by conventional methods and maintained at about 10° C., 9° C., 8° C., 7° C., 5° C., 4° C., 2° C., 2° C., 1° C., 0° C., or less. In some aspects, the washed chitosan core particles are stored at about 4° C.

The chitosan solution can be a suitable concentration such as about 0.5% (w/v), about 1% (w/v), about 1.5% (w/v), about 2% (w/v), about 2.5% (w/v), about 3% (w/v), about 3.5% (w/v), about 4% (w/v), about 4.5% (w/v), about 5% (w/v), about 5.5% (w/v), about 6% (w/v), about 6.5% (w/v), about 7% (w/v), about 7.5% (w/v), about 8% (w/v), about 8.5% (w/v), about 9% (w/v), about 9.5% (w/v), about 10% (w/v), about 10.5% (w/v), 11% (w/v), about 11.5% (w/v), about 12% (w/v), about 12.5% (w/v), about 13% (w/v), about 13.5% (w/v), about 14% (w/v), about 14.5% (w/v), about 15% (w/v), about 15.5% (w/v), about 16% (w/v), about 16.5% (w/v), about 17% (w/v), about 17.5% (w/v), about 18% (w/v), about 18.5% (w/v), about 19% (w/v), about 19.5% (w/v), about 20% (w/v); any range encompassed by the foregoing w/v % values; or any combination of the foregoing w/v % values. The solvent system can aqueous, or a buffered aqueous solution, e.g., an acetic acid/sodium acetate buffer solutions at a pH of about 3.0, 3.1, 3.2, 3.3, 3.3., 3.5, 3.6, 3.7, 3.8, 3.9, 4.0, 4.1, 4.2, 4.3, 4.4., 4.5, 4.6, 4.7, 4.8, 4.9, 5.0, 5.1, 5.2, 5.3, 5.5., 5.5, 5.6, 5.7, 5.8, 5.9, 6.0, 6.1, 6.2, 6.3, 6.6., 6.5, 6.6, 6.7, 6.8, 6.9, 7.0; any range encompassed by the foregoing pH values; or any combination of the foregoing pH values. In some aspects, the pH of the solution is adjusted to maintain optimal therapeutic potency of the therapeutic agent.

The buffer can be any suitable buffer compatible with the chitosan and the one or more therapeutic agents, e.g., but not limited to, an acetic acid/acetate buffer system, an citric acid/citrate buffer system, a HEPES buffer system, and the like.

In various aspects, the total w/v percent representing the w/v percent sum for the chitosan and the one or more therapeutic agents is equal to the range of w/v percent given for chitosan alone above. In some aspects, the mass ratio of chitosan to the one or more therapeutic agents is about 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2.1:1, 2.2:1, 2.3:1, 2.4:1, 2.5:1, 2.6:1, 2.7:1, 2.8:1, 2.9:1, 3.1:1, 3.2:1, 3.3:1, 3.4:1, 3.5:1, 3.6:1, 3.7:1, 3.8:1, 3.9:1, 4.1:1, 4.2:1, 4.3:1, 4.4:1, 4.5:1, 4.6:1, 4.7:1, 4.8:1, 4.9:1, 5:1; any range encompassed by the foregoing mass ratio values; or any combination of the foregoing mass ratios.

In an exemplary aspect, the oil phase for preparation of the chitosan core via the water-in-oil emulsion method can be any suitable oil, oil mixture, or oil solution. For example, in some aspects, the oil phase can be a mixture of liquid paraffin and petroleum ether, e.g., at a volume/volume ratio of about 1:1, 1:2, 1:3, 1:4, 1:5, 1:6, 1:7, 1:8, 1:9, 2:1, 2:2, 2:3, 2:4, 2:5, 2:6, 2:7, 2:8, 2:9, 3:1, 3:2, 3:3, 3:4, 3:5, 3:6, 3:7, 3:8, 3:9, 4:1, 4:2, 4:3, 4:4, 4:5, 4:6, 4:7, 4:8, 4:9, 5:1, 5:2, 5:3, 5:4, 5:5, 5:6, 5:7, 5:8, 5:9, 6:1, 6:2, 6:3, 6:4, 6:5, 6:6, 6:7, 6:8, 6:9, 7:1, 7:2, 7:3, 7:4, 7:5, 7:6, 7:7, 7:8, 7:9, 8:1, 8:2, 8:3, 8:4, 8:5, 8:6, 8:7, 8:8, 8:9, 9:1, 9:2, 9:3, 9:4, 9:5, 9:6, 9:7, 9:8, 9:9, 10:1; any range encompassed by the foregoing volume/volume ratios; or any combination of the foregoing volume/volume ratios.

In various aspects, the one or more surfactant in the oil phase used in the preparation of the chitosan core can be present in an amount of about about 0.5% wt %, about 1% wt %, about 1.5% wt %, about 2% wt %, about 2.5% wt %, about 3% wt %, about 3.5% wt %, about 4% wt %, about 4.5% wt %, about 5% wt %, about 5.5% wt %, about 6% wt %, about 6.5% wt %, about 7% wt %, about 7.5% wt %, about 8% wt %, about 8.5% wt %, about 9% wt %, about 9.5% wt %, about 10% wt %, about 10.5% wt %, 11% wt %, about 11.5% wt %, about 12% wt %, about 12.5% wt %, about 13% wt %, about 13.5% wt %, about 14% wt %, about 14.5% wt %, about 15% wt %, about 15.5% wt %, about 16% wt %, about 16.5% wt %, about 17% wt %, about 17.5% wt %, about 18% wt %, about 18.5% wt %, about 19% wt %, about 19.5% wt %, about 20% wt %; any range encompassed by the foregoing wt % values; or any combination of the foregoing wt % values.

In some aspects, the one or more surfactant in the oil phase used in the preparation of the chitosan core can be a suitable surfactant such as, but not limited to, IPEGAL® CO-520, Span® 80, bovine serum albumin (BSA), or PEG. In a further aspect, the PEG, can have a structure shown by the formula below:

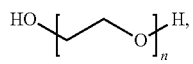

where n is about 300 to about 6000. In some aspects, n is about 300. In further aspects, n is about 6000. In various aspects, the use of a surfactant is used in an amount effective in the preparation solution to reduce the surface tension in the preparation solution compared to a preparation solution without surfactant by about 10%, about 15%, about 20%, about 25%, about 30%, about 35%, about 40%, about 45%, about 50%, about 55%, about 60%, about 65%; any range encompassed by the foregoing values; or any set of the foregoing values.

In various aspects, aqueous solution comprising the chitosan and the one or more therapeutic agents in a suitable solvent or buffer solution can be dispersed into the oil phase at a volume/volume ratio of about 1:1, 1:2, 1:3, 1:4, 1:5, 1:6, 1:7, 1:8, 1:9, 2:1, 2:2, 2:3, 2:4, 2:5, 2:6, 2:7, 2:8, 2:9, 3:1, 3:2, 3:3, 3:4, 3:5, 3:6, 3:7, 3:8, 3:9, 4:1, 4:2, 4:3, 4:4, 4:5, 4:6, 4:7, 4:8, 4:9, 5:1, 5:2, 5:3, 5:4, 5:5, 5:6, 5:7, 5:8, 5:9, 6:1, 6:2, 6:3, 6:4, 6:5, 6:6, 6:7, 6:8, 6:9, 7:1, 7:2, 7:3, 7:4, 7:5, 7:6, 7:7, 7:8, 7:9, 8:1, 8:2, 8:3, 8:4, 8:5, 8:6, 8:7, 8:8, 8:9, 9:1, 9:2, 9:3, 9:4, 9:5, 9:6, 9:7, 9:8, 9:9, 10:1; any range encompassed by the foregoing volume/volume ratios; or any combination of the foregoing volume/volume ratios.

In various aspects, the crosslinking agent added to the aqueous solution comprising the chitosan and the one or more therapeutic agents in a suitable solvent or buffer solution that has been dispersed into the oil phase is a cross-linking agent comprising cross-linkable aldehyde groups. For example, glutaraldehyde can be used, but the skilled artisan could choose other related types of cross-linking agents, i.e., comprising aldehyde groups cross-linkable to amino groups in chitosan under the preparation conditions described herein. In some aspects, the cross-linking agent is added at a molar ratio of aldehyde groups of glutaraldehyde to amino groups of chitosan of about 0.1:1, 0.1:2, 0.1:3, 0.1:4, 0.1:5, 0.1:6, 0.1:7, 0.1:8, 0.1:9, 0.2:1, 0.2:2, 0.2:3, 0.2:4, 0.2:5, 0.2:6, 0.2:7, 0.2:8, 0.2:9, 0.3:1, 0.3:2, 0.3:3, 0.3:4, 0.3:5, 0.3:6, 0.3:7, 0.3:8, 0.3:9, 0.4:1, 0.4:2, 0.4:3, 0.4:4, 0.4:5, 0.4:6, 0.4:7, 0.4:8, 0.4:9, 0.5:1, 0.5:2, 0.5:3, 0.5:4, 0.5:5, 0.5:6, 0.5:7, 0.5:8, 0.5:9, 0.6:1, 0.6:2, 0.6:3, 0.6:4, 0.6:5, 0.6:6, 0.6:7, 0.6:8, 0.6:9, 0.7:1, 0.7:2, 0.7:3, 0.7:4, 0.7:5, 0.7:6, 0.7:7, 0.7:8, 0.7:9, 0.8:1, 0.8:2, 0.8:3, 0.8:4, 0.8:5, 0.8:6, 0.8:7, 0.8:8, 0.8:9, 0.9:1, 0.9:2, 0.9:3, 0.9:4, 0.9:5, 0.9:6, 0.9:7, 0.9:8, 0.9:9, 1:1, 1:2, 1:3, 1:4, 1:5, 1:6, 1:7, 1:8, 1:9, 2:1, 2:2, 2:3, 2:4, 2:5, 2:6, 2:7, 2:8, 2:9, 3:1, 3:2, 3:3, 3:4, 3:5, 3:6, 3:7, 3:8, 3:9, 4:1, 4:2, 4:3, 4:4, 4:5, 4:6, 4:7, 4:8, 4:9, 5:1, 5:2, 5:3, 5:4, 5:5, 5:6, 5:7, 5:8, 5:9, 6:1, 6:2, 6:3, 6:4, 6:5, 6:6, 6:7, 6:8, 6:9, 7:1, 7:2, 7:3, 7:4, 7:5, 7:6, 7:7, 7:8, 7:9, 8:1, 8:2, 8:3, 8:4, 8:5, 8:6, 8:7, 8:8, 8:9, 9:1, 9:2, 9:3, 9:4, 9:5, 9:6, 9:7, 9:8, 9:9, 10:1; any range encompassed by the foregoing molar ratios; or any combination of the foregoing molar ratios.

In some aspects, the chitosan core-shell material particles can be prepared using an oil-in-water emulsion method. For example, the method can comprising preparing a shell material solution comprising a shell material, e.g., PCL, at a suitable concentration, e.g., about 0.001 g shell material to about 1.0 g shell material, in a suitable solvent, e.g., acetone, in a suitable volume, e.g., about 1 mL solvent to about 10 mL solvent, at a suitable temperature, e.g., about 40° C. to about 60° C., for a suitable period of time, e.g., sufficient to effect complete dissolution of the shell material, and then cooled to a suitable temperature, e.g., about 20° C. to about 60° C. Next, a shell material-chitosan core particle solution is prepared by adding to the foregoing shell material solution the chitosan core particles (prepared as disclosed herein, and comprising no therapeutic agent or one or more therapeutic agents), in a suitable solvent at a suitable concentration, e.g., about 0.001 g to about 1.0 g chitosan core particles per milliliter of solvent, at suitable rate of addition, e.g., about 0.01 mL/min to about 10 mL/min, with stirring for a period of time sufficient to effect homogeneity of the chitosan core particles in the shell material solution. To the foregoing shell material-chitosan core particle solution is added one or more surfactants at a suitable concentration, e.g., about 1 μL to about 100 μL of CO-520 per about 0.1 mL to about 10 mL shell material-chitosan core particle solution. Other surfactants can be used at a similar molar amount of another surfactant based on the conventional density of CO-520. Alternatively, the amount of surfactant used can be an amount sufficient to achieve a desired reduction in surface tension of the shell material-chitosan core particle solution. Separately, a water phase is prepared using water or a suitable aqueous buffered solution. The water phase can further comprise a surfactant, e.g., about 0.1 mL CO-520 to about 10 mL CO-520 in a volume of water or buffered aqueous solution of about 25 mL to about 50 mL. The shell material-chitosan core particle solution is added to the water phase at a suitable feed rate, e.g., about 0.01 mL/min to about 10 mL/min, with continuous stirring for a period of time sufficient to effect homogeneity of the oil-in-water phase emulsion thus created, for a suitable period of period of time, e.g., about 10 minutes to about 10 hours. The chitosan core-shell material particles can be isolated by any suitable method, e.g., centrifugation. Following centrifugation, the chitosan core-shell material particles are washed with one or more solvents one or more times. For example, the chitosan core-shell material particles can be washed sequentially with solvents such as water, an alcohol, and mixtures thereof. Washing is understood to comprise suspending isolated chitosan core-shell material particles in a solvent, mixing, and then collecting the chitosan core-shell material particles by centrifugation. In a particular aspect, the chitosan core-shell material particles can be washed with water, then with isopropanol. For storage, the washed chitosan core-shell material particles can be freeze dried by conventional methods and maintained at about 10° C., 9° C., 8° C., 7° C., 5° C., 4° C., 2° C., 2° C., 1° C., 0° C., or less. In some aspects, the freeze-dried chitosan core-shell material particles are stored at about 4° C.

In various aspects, the one or more surfactant in the oil phase and the shell material-chitosan particle solution used in the preparation of the chitosan core-shell material particles can be present in an amount of about 0.001% wt %, about 0.002% wt %, about 0.003% wt %, about 0.004% wt %, about 0.005% wt %, about 0.006% wt %, about 0.007% wt %, about 0.008% wt %, about 0.009% wt %, about 0.01% wt %, about 0.02% wt %, about 0.03% wt %, about 0.04% wt %, about 0.05% wt %, about 0.06% wt %, about 0.07% wt %, about 0.08% wt %, about 0.09% wt %, about 0.1% wt %, about 0.2% wt %, about 0.3% wt %, about 0.4% wt %, about 0.5% wt %, about 0.6% wt %, about 0.7% wt %, about 0.8% wt %, about 0.9% wt %, about 1% wt %, about 1.5% wt %, about 2% wt %, about 2.5% wt %, about 3% wt %, about 3.5% wt %, about 4% wt %, about 4.5% wt %, about 5% wt %, about 5.5% wt %, about 6% wt %, about 6.5% wt %, about 7% wt %, about 7.5% wt %, about 8% wt %, about 8.5% wt %, about 9% wt %, about 9.5% wt %, about 10% wt %, about 10.5% wt %, 11% wt %, about 11.5% wt %, about 12% wt %, about 12.5% wt %, about 13% wt %, about 13.5% wt %, about 14% wt %, about 14.5% wt %, about 15% wt %, about 15.5% wt %, about 16% wt %, about 16.5% wt %, about 17% wt %, about 17.5% wt %, about 18% wt %, about 18.5% wt %, about 19% wt %, about 19.5% wt %, about 20% wt %; any range encompassed by the foregoing wt % values; or any combination of the foregoing wt % values.

In various aspects, the one or more surfactant in the oil phase and the shell material-chitosan particle solution used in the preparation of the chitosan core-shell material particles can be present in an amount of about 0.001% v/v %, about 0.002% v/v %, about 0.003% v/v %, about 0.004% v/v %, about 0.005% v/v %, about 0.006% v/v %, about 0.007% v/v %, about 0.008% v/v %, about 0.009% v/v %, about 0.01% v/v %, about 0.02% v/v %, about 0.03% v/v %, about 0.04% v/v %, about 0.05% v/v %, about 0.06% v/v %, about 0.07% v/v %, about 0.08% v/v %, about 0.09% v/v %, about 0.1% v/v %, about 0.2% v/v %, about 0.3% v/v %, about 0.4% v/v %, about 0.5% v/v %, about 0.6% v/v %, about 0.7% v/v %, about 0.8% v/v %, about 0.9% v/v %, about 1% v/v %, about 1.5% v/v %, about 2% v/v %, about 2.5% v/v %, about 3% v/v %, about 3.5% v/v %, about 4% v/v %, about 4.5% v/v %, about 5% v/v %, about 5.5% v/v %, about 6% v/v %, about 6.5% v/v %, about 7% v/v %, about 7.5% v/v %, about 8% v/v %, about 8.5% v/v %, about 9% v/v %, about 9.5% v/v %, about 10% v/v %, about 10.5% v/v %, 11% v/v %, about 11.5% v/v %, about 12% v/v %, about 12.5% v/v %, about 13% v/v %, about 13.5% v/v %, about 14% v/v %, about 14.5% v/v %, about 15% v/v %, about 15.5% v/v %, about 16% v/v %, about 16.5% v/v %, about 17% v/v %, about 17.5% v/v %, about 18% v/v %, about 18.5% v/v %, about 19% v/v %, about 19.5% v/v %, about 20% v/v %; any range encompassed by the foregoing v/v % values; or any combination of the foregoing v/v % values In some aspects, the one or more surfactant in the oil phase used in the preparation of the chitosan core can be a suitable surfactant such as, but not limited to, IPEGAL® CO-520, Span® 80, bovine serum albumin (BSA), or PEG. In a further aspect, the PEG, can have a structure shown by the formula below:

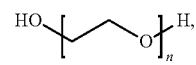

where n is about 300 to about 6000. In some aspects, n is about 300. In further aspects, n is about 6000. In various aspects, the use of a surfactant is used in an amount effective in the preparation solution to reduce the surface tension in the preparation solution compared to a preparation solution without surfactant by about 10%, about 15%, about 20%, about 25%, about 30%, about 35%, about 40%, about 45%, about 50%, about 55%, about 60%, about 65%; any range encompassed by the foregoing values; or any set of the foregoing values.

In various aspects, the shell material-chitosan core particle solution be dispersed into the water phase at a volume/volume ratio of about 1:1, 1:2, 1:3, 1:4, 1:5, 1:6, 1:7, 1:8, 1:9, 2:1, 2:2, 2:3, 2:4, 2:5, 2:6, 2:7, 2:8, 2:9, 3:1, 3:2, 3:3, 3:4, 3:5, 3:6, 3:7, 3:8, 3:9, 4:1, 4:2, 4:3, 4:4, 4:5, 4:6, 4:7, 4:8, 4:9, 5:1, 5:2, 5:3, 5:4, 5:5, 5:6, 5:7, 5:8, 5:9, 6:1, 6:2, 6:3, 6:4, 6:5, 6:6, 6:7, 6:8, 6:9, 7:1, 7:2, 7:3, 7:4, 7:5, 7:6, 7:7, 7:8, 7:9, 8:1, 8:2, 8:3, 8:4, 8:5, 8:6, 8:7, 8:8, 8:9, 9:1, 9:2, 9:3, 9:4, 9:5, 9:6, 9:7, 9:8, 9:9, 10:1; any range encompassed by the foregoing volume/volume ratios; or any combination of the foregoing volume/volume ratios.

In various aspects, the shell material can be a suitable biocompatible polymer such as poly(lactide-co-glycolide) (PLGA), poly caprolactone (PCL), poly(lactic acid) (PLA), poly(glycolic acid) (PGA), polyethylene glycol, polysorbate, poly(ε-caprolactone-co-ethyl ethylene phosphate) (PCLEEP), polyvinyl alcohol (PVA), and combinations thereof. In certain aspects, the shell material comprises a biocompatible polymer selected from as poly(lactide-co-glycolide) (PLGA), poly caprolactone (PCL), poly(lactic acid) (PLA), poly(glycolic acid) (PGA), and combinations thereof. In a further aspect, the shell material comprises a biocompatible polymer selected from poly(lactide-co-glycolide) (PLGA), poly caprolactone (PCL), poly(lactic acid) (PLA), and combinations thereof. In a still further aspect, the shell material comprises poly(lactide-co-glycolide) (PLGA). In a yet further aspect, the shell material comprises, poly caprolactone (PCL). In an even further aspect, the shell material comprises poly(lactic acid) (PLA).

Methods of Treating a Clinical Condition Using a Disclosed Drug Delivery Composition Disclosed herein are methods of treating a clinical condition by administration of a disclosed drug delivery composition. A clinical condition can be a clinical disorder, disease, dysfunction or other condition that can be ameliorated by a therapeutic intervention.

The term "administering" or "administration" of a disclosed drug delivery composition to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another. In some instances, administration is via injection to the eye, including intraocular injection. In other instances, for example, in treatment of a cancer, administration can be via injection of a disclosed drug delivery composition within, abutting, adjacent, or proximal to a tumor or other mass of cancer cells.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

The term "separate" administration refers to an administration of at least two active ingredients at the same time or substantially the same time by different routes.

The term "sequential" administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. The term "sequential" therefore is different than "simultaneous" administration.

The term "simultaneous" administration refers to the administration of at least two active ingredients by the same route at the same time or at substantially the same time.

The term "therapeutic" as used herein means a treatment and/or prophylaxis. A therapeutic effect is obtained by suppression, remission, or eradication of a disease state.

Age-related macular degeneration (AMD) is the fourth most common causes of blindness. The excess expression of vascular endothelium growth factor (VEGF) stimulates the neovascularization in choroid. These abnormal blood vessels will break through the Bruch's membrane towards macular. Once the blood vessels bleed and scar due to their fragile structure, it will bring irreversible damage to the photoreceptors and retina. For current treatment, monthly vitreous injection of anti-VEGF therapeutic agents such as bevacizumab and ranibizumab is given to block VEGF from initiating the angiogenesis. However, frequent injections can lead to infection, elevated intraocular pressure and rhegmatogenous retinal detachment. Moreover, current treatment methods involving monthly intraocular injections has been found to lower patient compliance and increase the cost medical care associated with these diseases.

To address the problems associated with the current clinical treatment of eye disease, the present disclosure provides novel drug delivery compositions and methods for delivery of therapeutic agents to the eye. The disclosed drug delivery compositions comprise two polymeric materials, including a first polymer comprising cationic moieties in the polymer backbone and a second polymer that is biodegradable under physiological conditions. In various aspects, the disclosed compositions comprise a core component comprising the first polymer, and a shell layer comprising the second polymer such that the shell layer surrounds the core component. The structure and polymers used in the disclosed drug delivery compositions provide an extended period of drug release and also avoids the side effects associated with the monthly injections to the eye, e.g., such as the current standard of care involving monthly injections of anti-VEGF therapeutic agents. In a further aspect, the disclosed drug delivery compositions comprise microparticles comprising the disclosed compositions. The first polymer or core component, without wishing to be bound by a particular theory, is believed to be responsible for appropriate diffusion of a therapeutic agent, such as an anti-VEGF therapeutic, including a protein or antibody, by the electrostatic attraction. Further, without wishing to be bound by a particular theory, it is believed that the function of the second polymer forming the shell or outer layer provides modulated biodegradation and helps to maintain structural integrity. The preliminary results disclosed in the herewith filed appendices demonstrate that the disclosed drug delivery compositions comprising two polymers enable longer-term local drug administration as compared to previously reported devices. Accordingly, the disclosed drug delivery compositions provide a novel and effective method to raise the therapeutic efficacy and further improve the quality of life for people diagnosed with eye diseases such as wet AMD.

In various aspects, compared to previously known particle drug delivery systems for the eye, the disclosed drug delivery systems and compositions have a multilayered core-shell structure which can retain a therapeutic agent over a longer period of time, including such therapeutic agents as anti-VEGF therapeutics. In some aspects, the particle core can be prepared using chitosan. Without wishing to be bound by a particular theory, it is believed that the positively charged backbone of chitosan ionically interacts with the negatively charged therapeutic agents, such as anti-VEGF therapeutic agents, and thereby control the diffusion of drug. In a further aspect, polycaprolactone (PCL) or polylactic-co-glycolic acid) (PLGA) can be used in the shell layer. Without wishing to be bound by a particular theory, it is believed that a polymer such as PCL or PLGA in the shell layer can modulate biodegradation of the particle, and thereby modulate the rate of drug during the particle erosion or biodegradation. In a further aspect, a polymer, such as PCL or PLGA, can be deposited on the surface of core polymer using a nonionic surfactant, thereby providing a nanoporous shell structure. It is believed, without wishing to be bound by a particular theory, that a nanoporous shell structure provides a structure capable of achieving zero-order release kinetics. In a still further aspect, the particles of the disclosed drug delivery compositions and systems can be about 15 µm in powder form. In a yet further aspect, the disclosed drug delivery compositions in the form of dry powder can be dissolved in phosphate buffer saline, thereby providing a solution capable of being injected into vitreous humor via 30-gauge needle.

In various aspects, the disclosed methods pertain to a method of treating an ophthalmological disorder, the method comprising injecting a therapeutically effective amount of a disclosed drug delivery composition into an eye of a subject. The subject can be a patient; and the patient can have been diagnosed with an ophthalmological disorder. In some instances, the method can further comprise diagnosing a subject with an ophthalmological disorder.

The ophthalmological disorder can be acute macular neuroretinopathy; Behcet's disease; neovascularization, including choroidal neovascularization; diabetic uveitis; histoplasmosis; infections, such as fungal or viral-caused infections; macular degeneration, such as acute macular degeneration (AMC)), including wet, AMD, non-exudative, AMD and exudative AMD; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, a cancer, and glaucoma. In certain instances, the ophthalmological disorder is wet age-related macular degeneration (wet AMD), a cancer, neovascularization, macular edema, or edema. In a further particular aspect, the ophthalmological disorder is wet age-related macular degeneration (wet AMD).

In various aspects, the injection for treatment of an ophthalmological disorder can be injection to the vitreous chamber of the eye. In some cases, the injection is an intravitreal injection, a subconjunctival injection, a subtenon injection, a retrobulbar injection, or a suprachoroidal injection.

In various aspects, the method for treatment of an ophthalmological disorder comprises administration of a disclosed drug delivery composition in an amount, e.g., via injection of about 0.1 mg to about 25 mg of therapeutic agent; or about 1 mg to about 15 mg of therapeutic agent.

"Ocular region" or "ocular site" means any area of the ocular globe (eyeball), including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include, but are not limited to, the anterior chamber, the posterior chamber, the vitreous cavity, the choroid, the suprachoroidal space, the conjunctiva, the subconjunctival space, the episcieral space, the intracorneal space, the subretinal space, sub-Tenon's space, the epicorneal space, the sclera, the pars plana, surgically-induced avascular regions, the macula, and the retina.

"Ophthalmological disorder" can mean a disease, ailment or condition which affects or involves the eye or one of the parts or regions of the eye. Broadly speaking, the eye includes the eyeball, including the cornea, and other tissues and fluids which constitute the eyeball, the periocular muscles (such as the oblique and rectus muscles) and the portion of the optic nerve which is within or adjacent to the eyeball.

"Glaucoma" means primary, secondary and/or congenital glaucoma. Primary glaucoma can include open angle and closed angle glaucoma. Secondary glaucoma can occur as a complication of a variety of other conditions, such as injury, inflammation, pigment dispersion, vascular disease and diabetes. The increased pressure of glaucoma causes blindness because it damages the optic nerve where it enters the eye.

Thus, in one non-limiting embodiment, by lowering reactive oxygen species, STC-1, or MSCs which express increased amounts of STC-1, may be employed in the treatment of glaucoma and prevent or delay the onset of blindness.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic retinopathy, uveitis, proliferative vitreoretinopathy (PVR), sympathetic ophthalmia, Vogt-Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation, as well as tissue injuries caused by means other than inflammation, such as chemical injury, including chemical burns, as well as injuries caused by infections, including but not limited to, bacterial, viral, or fungal infections.

"Intraocular" means within or under an ocular tissue. An intraocular administration of a drug delivery system includes administration of the drug delivery system to a sub-tenon, subconjunctival, suprachoroidal, subretinal, intravitreal, anterior chamber, and the like location. An intraocular administration of a drug delivery system excludes administration of the drug delivery system to a topical, systemic, intramuscular, subcutaneous, intraperitoneal, and the like location.

"Macular degeneration" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and capillary endothelial cells. Age-related macular degeneration, or ARMD, is the major macular degeneration related condition, but a number of others are known including, but not limited to, Best macular dystrophy, Stargardt macular dystrophy, Sorsby fundus dystrophy, Mallatia Leventinese, Doyne honeycomb retinal dystrophy, and RPE pattern dystrophies. Age-related macular degeneration (AMD) is described as either "dry" or "wet." The wet, exudative, neovascular form of AMD affects about 10-20% of those with AMD and is characterized by abnormal blood vessels growing under or through the retinal pigment epithelium (RPE), resulting in hemorrhage, exudation, scarring, or serous retinal detachment. Eighty to ninety percent of AMD patients have the dry form characterized by atrophy of the retinal pigment epithelium and loss of macular photoreceptors. Drusen may or may not be present in the macula. There may also be geographic atrophy of retinal pigment epithelium in the macula accounting for vision loss. At present there is no cure for any form of AMD, although some success in attenuation of wet AMD has been obtained with photodynamic and especially anti-VEGF therapy.

"Drusen" is debris-like material that accumulates with age below the RPE. Drusen is observed using a funduscopic eye examination. Normal eyes may have maculas free of drusen, yet drusen may be abundant in the retinal periphery. The presence of soft drusen in the macula, in the absence of any loss of macular vision, is considered an early stage of AMD. Drusen contains a variety of lipids, polysaccharides, and glycosaminoglycans along with several proteins, modified proteins or protein adducts. There is no generally accepted therapeutic method that addresses drusen formation and thereby manages the progressive nature of AMD.

"Ocular neovascularization" (ONV) is used herein to refer to choroidal neovascularization or retinal neovascularization, or both.

"Retinal neovascularization" (RNV) refers to the abnormal development, proliferation, and/or growth of retinal blood vessels, e.g., on the retinal surface.

"Subretinal neovascularization" (SRNVM) refers to the abnormal development, proliferation, and/or growth of blood vessels beneath the surface of the retina.

"Cornea" refers to the transparent structure forming the anterior part of the fibrous tunic of the eye. It consists of five layers, specifically: 1) anterior corneal epithelium, continuous with the conjunctiva; 2) anterior limiting layer (Bowman's layer); 3) substantia propria, or stromal layer; 4) posterior limiting layer (Descemet's membrane); and 5) endothelium of the anterior chamber or keratoderma.

"Retina" refers to the innermost layer of the ocular globe surrounding the vitreous body and continuous posteriorly with the optic nerve. The retina is composed of layers including the: 1) internal limiting membrane; 2) nerve fiber layer; 3) layer of ganglion cells; 4) inner plexiform layer; 5) inner nuclear layer; 6) outer plexiform layer; 7) outer nuclear layer; 8) external limiting membrane; and 9) a layer of rods and cones.

"Retinal degeneration" refers to any hereditary or acquired degeneration of the retina and/or retinal pigment epithelium. Non-limiting examples include retinitis pigmentosa, Best's Disease, RPE pattern dystrophies, and age-related macular degeneration.

In various aspects, a method of treating an ophthamological disorder such as various ocular diseases or conditions of the retina, including the following: maculopathies/retinal degeneration: macular degeneration, including age-related macular degeneration (ARMD), such as non-exudative age-related macular degeneration and exudative age-related macular degeneration; choroidal neovascularization; retinopathy, including diabetic retinopathy, acute and chronic macular neuroretinopathy, central serous chorioretinopathy; and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, Lyme Disease, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease, Traumatic/surgical diseases: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, ocular histoplasmosis syndrome (OHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Best's disease, pattern dystrophy of the retinal pigment epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigment epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

An anterior ocular condition is a disease, ailment or condition which affects or which involves an anterior (i.e., front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis, including, but not limited to, atopic keratoconjunctivitis; corneal injuries, including, but not limited to, injury to the corneal stromal areas; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

Other diseases or disorders of the eye which may be treated in accordance with the present invention include, but are not limited to, ocular cicatricial pemphigoid (OCP), Stevens Johnson syndrome and cataracts.

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e., the optic disc), and blood vessels and nerves which vascularize or innervate a posterior ocular region or site. Thus, a posterior ocular condition can include a disease, ailment or condition, such as for example, acute macular neuroretinopathy; Behcet's disease; choroidal neovascularization; diabetic retinopathy; uveitis; ocular histoplasmosis; infections, such as fungal or viral-caused infections; macular degeneration, such as acute macular degeneration, non-exudative age-related macular degeneration and exudative age-related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial or venous occlusive disease, retinal detachment, uveitic retinal disease; sympathetic ophthalmia; Vogt-Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal ganglion cells or retinal nerve fibers (i.e., neuroprotection).

In some embodiments, the ophthalmic disorder is ocular inflammation resulting from, e.g., iritis, conjunctivitis, seasonal allergic conjunctivitis, acute and chronic endophthalmitis, anterior uveitis, uveitis associated with systemic diseases, posterior segment uveitis, chorioretinitis, pars planitis, masquerade syndromes including ocular lymphoma, pemphigoid, scleritis, keratitis, severe ocular allergy, corneal abrasion and blood-aqueous barrier disruption. In yet another embodiment, the ophthalmic disorder is post-operative ocular inflammation resulting from, for example, photorefractive keratectomy, cataract removal surgery, intraocular lens implantation, vitrectomy, corneal transplantation, forms of lamellar keratectomy (DSEK, etc), and radial keratotomy.

In various aspects, the disclosed drug delivery compositions used in the method of treating an ophthamological disorder is an agent for use in the treatment of eye disease such as beta-blockers including timolol, betaxolol, levobetaxolol, carteolol, miotics including pilocarpine, carbonic anhydrase inhibitors, prostaglandins, serotonergics, muscarinics, dopaminergic agonists, adrenergic agonists including apraclonidine and brimonidine; anti-angiogenesis agents; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as EGF; immunosuppressant agents; and anti-allergic agents including olopatadine; prostaglandins such as latanoprost; 15-keto latanoprost; travoprost; and unoprostone isopropyl.

In various aspects, the disclosed drug delivery compositions used in the method of treating an ophthamological disorder is an agent for use in the treatment of eye disease such as an effective amount of an agent selected from the group consisting of an anti-inflammatory agent, a calcineurin inhibitor, an antibiotic, a nicotinic acetylcholine receptor agonist, and an anti-lymphangiogenic agent.

In some examples, the anti-inflammatory agent may be cyclosporine. The calcineurin inhibitor may be voclosporin. The antibiotic may be selected from the group consisting of, amikacin, gentamycin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, sulfacetamide, sulfamethizole, sulfasalazine, sulfisoxazole, trimethoprim, cotrimoxazole, demeclocycline, doxycycline, minocycline, oxytetracycline, and tetracycline. The nicotinic acetylcholine receptor agonist may be any of pilocarpine, atropine, nicotine, epibatidine, lobeline, or imidacloprid. The anti-lymphangiogenic agent may be a vascular endothelial growth factor C (VEGF-C) antibody, a VEGF-D antibody or a VEGF-3 antibody.

In various aspects, the disclosed drug delivery compositions used in the method of treating an ophthamological disorder is an agent for use in the treatment of eye disease such as beta-blockers, including levobunolol (BETAGAN), timolol (BETIMOL, TIMOPTIC), betaxolol (BETOPTIC) and metipranolol (OPTIPRANOLOL); alpha-agonists, such as apraclonidine (IOPIDINE) and brimonidine (ALPHAGAN); carbonic anhydrase inhibitors, such as acetazolamide, methazolamide, dorzolamide (TRUSOPT) and brinzolamide (AZOPT); prostaglandins or prostaglandin analogs such as latanoprost (XALATAN), bimatoprost (LUMIGAN) and travoprost (TRAVATAN); miotic or cholinergic agents, such as pilocarpine (ISOPTO CARPINE, PILOPINE) and carbachol (ISOPTO CARBACHOL); epinephrine compounds, such as dipivefrin (PROPINE); forskolin; or neuroprotective compounds, such as brimonidine and memantine. In certain embodiments, the compound used in combination with a compound against one of the identified targets, or pathways, is not an anti-angiogenic agent, such as a steroid derivative, such as 2-methoxyestradiol or analogs or derivatives thereof. In other embodiments, the additional therapeutic agent can be an antibiotic.

The term "VEGF" refers to a vascular endothelial growth factor that induces angiogenesis or an angiogenic process, including, but not limited to, increased permeability. As used herein, the term "VEGF" includes the various subtypes of VEGF (also known as vascular permeability factor (VPF) and VEGF-A) that arise by, e.g., alternative splicing of the VEGF-A/VPF gene including VEGF121, VEGF165 and VEGF189. Further, as used herein, the term "VEGF" includes VEGF-related angiogenic factors such as PlGF (placental growth factor), VEGF-B, VEGF-C, VEGF-D and VEGF-E, which act through a cognate VEFG receptor (i.e., VEGFR) to induce angiogenesis or an angiogenic process. The term "VEGF" includes any member of the class of growth factors that binds to a VEGF receptor such as VEGFR-1 (Flt-1), VEGFR-2 (KDR/Flk-1), or VEGFR-3 (FLT-4). The term "VEGF" can be used to refer to a "VEGF" polypeptide or a "VEGF" encoding gene or nucleic acid.

The term "anti-VEGF agent" refers to an agent that reduces, or inhibits, either partially or fully, the activity or production of a VEGF. An anti-VEGF agent can directly or indirectly reduce or inhibit the activity or production of a specific VEGF such as VEGF165. Furthermore, "anti-VEGF agents" include agents that act on either a VEGF ligand or its cognate receptor so as to reduce or inhibit a VEGF-associated receptor signal. Non-limiting examples of "anti-VEGF agents" include antisense molecules, ribozymes or RNAi that target a VEGF nucleic acid; anti-VEGF aptamers, anti-VEGF antibodies to VEGF itself or its receptor, or soluble VEGF receptor decoys that prevent binding of a VEGF to its cognate receptor; antisense molecules, ribozymes, or RNAi that target a cognate VEGF receptor (VEGFR) nucleic acid; anti-VEGFR aptamers or anti-VEGFR antibodies that bind to a cognate VEGFR receptor; and VEGFR tyrosine kinase inhibitors.

The term "anti-RAS agent" or "anti-Renin Angiotensin System agent" refers to refers to an agent that reduces, or inhibits, either partially or fully, the activity or production of a molecule of the renin angiotensin system (RAS). Non-limiting examples of "anti-RAS" or "anti-Renin Angiotensin System" molecules are one or more of an angiotensin-converting enzyme (ACE) inhibitor, an angiotensin-receptor blocker, and a renin inhibitor.

The term "steroid" refers to compounds belonging to or related to the following illustrative families of compounds: corticosteroids, mineralicosteroids, and sex steroids (including, for example, potentially androgenic or estrogenic or anti-andogenic and anti-estrogenic molecules). Included among these are, for example, prednisone, prednisolone, methyl-prednisolone, triamcinolone, fluocinolone, aldosterone, spironolactone, danazol (otherwise known as OPTINA), and others.

The terms "peroxisome proliferator-activated receptor gamma agent," or "PPAR-γ agent," or "PPARG agent," or "PPAR-gamma agent" refers to agents which directly or indirectly act upon the peroxisome proliferator-activated receptor. This agent may also influence PPAR-alpha, "PPARA" activity.

In various aspects, the disclosed drug delivery compositions used in the method of treating an ophthamological disorder is an agent for use in the treatment of eye disease such as one or more of an anti-VEGF agent, an ACE inhibitor, a PPAR-gamma agonist or partial agonist, a renin inhibitor, a steroid, and an agent that modulates autophagy, as well as a semapimod, a MIF inhibitor, a CCR2 inhibitor, CKR-2B, a 2-thioimidazole, CAS 445479-97-0, CCX140, clodronate, a clodonate-liposome preparation or gadolinium chloride.

In various aspects, the disclosed drug delivery compositions used in the method of treating an ophthamological disorder is an agent for use in the treatment of eye disease such as a modulator of macrophage polarization. Illustrative modulators of macrophage polarization include peroxisome proliferator activated receptor gamma (PPAR-g) modulators, including, for example, agonists, partial agonists, antagonists or combined PPAR-gamma/alpha agonists.

In various aspects, the disclosed drug delivery compositions used in the method of treating an ophthamological disorder is an agent for use in the treatment of eye disease such as PPAR gamma modulator, including PPAR gamma modulators that are full agonists or a partial agonists. In some embodiments, the PPAR gamma modulator is a member of the drug class of thiazolidinediones (TZDs, or glitazones). By way of non-limiting example, the PPAR gamma modulator may be one or more of rosiglitazone (AVANDIA), pioglitazone (ACTOS), troglitazone (REZULIN), netoglitazone, rivoglitazone, ciglitazone, rhodanine. In some embodiments, the PPAR gamma modulator is one or more of irbesartan and telmesartan. In some embodiments, the PPAR gamma modulator is a nonsteroidal anti-inflammatory drugs (NSAID, such as, for example, ibuprofen) and indoles. Known inhibitors include the experimental agent GW-9662. Further examples of PPAR gamma modulators are described in WIPO Publication Nos. WO/1999/063983, WO/2001/000579, Nat Rev Immunol. 2011 Oct. 25; 11(11):750-61, or agents identified using the methods of WO/2002/068386, the contents of which are hereby incorporated by reference in their entireties.

In some embodiments, the PPAR gamma modulator is a "dual," or "balanced," or "pan" PPAR modulator. In some embodiments, the PPAR gamma modulator is a glitazar, which bind two or more PPAR isoforms, e.g., muraglitazar (Pargluva) and tesaglitazar (Galida) and aleglitazar.

In another embodiment, an agent of the invention is semapimod (CNI-1493) as described in Bianchi, et al. (March 1995). Molecular Medicine (Cambridge, Mass.) 1 (3): 254-266, the contents of which are hereby incorporated by reference in their entireties.

In various aspects, the disclosed drug delivery compositions used in the method of treating an ophthamological disorder is an agent for use in the treatment of eye disease such as is a migration inhibitory factor (MIF) inhibitor. Illustrative MIF inhibitors are described in WIPO Publication Nos. WO 2003/104203, WO 2007/070961, WO 2009/117706 and U.S. Pat. Nos. 7,732,146 and 7,632,505, and 7,294,753 7,294,753 the contents of which are hereby incorporated by reference in their entireties. In some embodiments, the MIF inhibitor is (S,R)-3-(4-hydroxyphenyl)-4,5-dihydro-5-isoxazole acetic acid methyl ester (ISO-1), isoxazoline, p 425 (J. Biol. Chem., 287, 30653-30663), epoxyazadiradione, or vitamin E.

In various aspects, the disclosed drug delivery compositions used in the method of treating an ophthamological disorder is an agent for use in the treatment of eye disease such as a chemokine receptor 2 (CCR2) inhibitor as described in, for example, U.S. patent and Patent Publication Nos.: U.S. Pat. Nos. 7,799,824, 8,067,415, US 2007/0197590, US 2006/0069123, US 2006/0058289, and US 2007/0037794, the contents of which are hereby incorporated by reference in their entireties. In some embodiments, the CCR2) inhibitor is Maraviroc, cenicriviroc, CD192, CCX872, CCX140, 2-((Isopropylaminocarbonyl)amino)-N-(2-((cis-2-((4-(methylthio)benzoyl)amino)cyclohexyl)amino)-2-oxoethyl)-5-(trifluoromethyl)-benzamide, vicriviroc, SCH351125, TAK779, Teijin, RS-504393, compound 2, compound 14, or compound 19 (Plos ONE 7(3): e32864).

In various aspects, the anti-VEGF agents useful in the present methods include ranibizumab, bevacizumab, aflibercept, KH902 VEGF receptor-Fc, fusion protein, 2C3 antibody, ORA102, pegaptanib, bevasiranib, SIRNA-027, decursin, decursinol, picropodophyllin, guggulsterone, PLG101, eicosanoid LXA4, PTK787, pazopanib, axitinib, CDDO-Me, CDDO-Imm, shikonin, beta-, hydroxyisovalerylshikonin, ganglioside GM3, DC101 antibody, Mab25 antibody, Mab73 antibody, 4A5 antibody, 4E10 antibody, 5F12 antibody, VA01 antibody, BL2 antibody, VEGF-related protein, sFLT01, sFLT02, Peptide B3, TG100801, sorafenib, G6-31 antibody, a fusion antibody and an antibody that binds to an epitope of VEGF. Additional non-limiting examples of anti-VEGF agents useful in the present methods include a substance that specifically binds to one or more of a human vascular endothelial growth factor-A (VEGF-A), human vascular endothelial growth factor-B (VEGF-B), human vascular endothelial growth factor-C (VEGF-C), human vascular endothelial growth factor-D (VEGF-D) and human vascular endothelial growth, factor-E (VEGF-E), and an antibody that binds, to an epitope of VEGF.

In various aspects, the anti-VEGF agent is the antibody ranibizumab or a pharmaceutically acceptable salt thereof. Ranibizumab is commercially available under the trademark LUCENTIS. In another embodiment, the anti-VEGF agent is the antibody bevacizumab or a pharmaceutically acceptable salt thereof. Bevacizumab is commercially available under the trademark AVASTIN. In another embodiment, the anti-VEGF agent is aflibercept or a pharmaceutically acceptable salt thereof. Aflibercept is commercially available under the trademark EYLEA. In one embodiment, the anti-VEGF agent is pegaptanib or a pharmaceutically acceptable salt thereof. Pegaptinib is commercially available under the trademark MACUGEN. In another embodiment, the anti-VEGF agent is an antibody or an antibody fragment that binds to an epitope of VEGF, such as an epitope of VEGF-A, VEGF-B, VEGF-C, VEGF-D, or VEGF-E. In some embodiments, the VEGF antagonist binds to an epitope of VEGF such that binding of VEGF and VEGFR are inhibited. In one embodiment, the epitope encompasses a component of the three dimensional structure of VEGF that is displayed, such that the epitope is exposed on the surface of the folded VEGF molecule. In one embodiment, the epitope is a linear amino acid sequence from VEGF.

In various aspects, the disclosed drug delivery compositions used in the method of treating an ophthamological disorder is an agent for use in the treatment of eye disease such as a renin angiotensin system (RAS) inhibitor. In some embodiments, the renin angiotensin system (RAS) inhibitor is one or more of an angiotensin-converting enzyme (ACE) inhibitor, an angiotensin-receptor blocker, and a renin inhibitor.

Non limiting examples of angiotensin-converting enzyme (ACE) inhibitors which are useful in the present invention include, but are not limited to: alacepril, alatriopril, altiopril calcium, ancovenin, benazepril, benazepril hydrochloride, benazeprilat, benzazepril, benzoylcaptopril, captopril, captoprilcysteine, captoprilglutathione, ceranapril, ceranopril, ceronapril, cilazapril, cilazaprilat, converstatin, delapril, delaprildiacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spirapril hydrochloride, temocapril, temocapril hydrochloride, teprotide, trandolapril, trandolaprilat, utibapril, zabicipril, zabiciprilat, zofenopril, zofenoprilat, pharmaceutically acceptable salts thereof, and mixtures thereof.

Non limiting examples of angiotensin-receptor blockers which are useful in the present invention include, but are not limited to: irbesartan (U.S. Pat. No. 5,270,317, hereby incorporated by reference in its entirety), candesartan (U.S. Pat. Nos. 5,196,444 and 5,705,517 hereby incorporated by reference in their entirety), valsartan (U.S. Pat. No. 5,399,578, hereby incorporated by reference in its entirety), and losartan (U.S. Pat. No. 5,138,069, hereby incorporated by reference in its entirety).

Non limiting examples of renin inhibitors which are useful in the present invention include, but are not limited to: aliskiren, ditekiren, enalkiren, remikiren, terlakiren, ciprokiren and zankiren, pharmaceutically acceptable salts thereof, and mixtures thereof.

In various aspects, the disclosed drug delivery compositions used in the method of treating an ophthamological disorder is an agent for use in the treatment of eye disease such as a steroid. In some embodiments, a steroid is a compound belonging to or related to the following illustrative families of compounds: corticosteroids, mineralicosteroids, and sex steroids (including, for example, potentially androgenic or estrogenic or anti-andogenic and anti-estrogenic molecules). Included amongst these are, by way of non-limiting example, prednisone, prednisolone, methylprednisolone, triamcinolone, fluocinolone, aldosterone, spironolactone, danazol (otherwise known as OPTINA), and others.

In various aspects, the disclosed drug delivery compositions used in the method of treating an ophthamological disorder is an agent for use in the treatment of eye disease such as an agent that modulates autophagy, microautophagy, mitophagy or other forms of autophagy. In some embodiments, the candidate drug and/or compound is one or more of sirolimus, tacrolimis, rapamycin, everolimus, bafilomycin, chloroquine, hydroxychloroquine, spautin-1, metformin, perifosine, resveratrol, trichostatin, valproic acid, Z-VAD-FMK, or others known to those in the art. Without wishing to be bound by theory, agent that modulates autophagy, microautophagy, mitophagy or other forms of autophagy may alter the recycling of intra-cellular components, for example, but not limited to, cellular organelles, mitochondria, endoplasmic reticulum, lipid or others. Without further wishing to be bound by theory, this agent may or may not act through microtubule-associated protein 1A/1B-light chain 3 (LC3).

In various aspects, the disclosed drug delivery compositions can be used to treat a cancer. As such, the disclosed drug delivery composition can comprise one or more cancer drug or anti-cancer agent. Exemplary cancer drugs can be selected from antimetabolite anti-cancer agents and antimitotic anti-cancer agents, and combinations thereof, to a subject. Various antimetabolite and antimitotic anti-cancer agents, including single such agents or combinations of such agents, may be employed in the methods and compositions described herein.

Antimetabolic anti-cancer agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one aspect, therefore, the antimetabolite anti-cancer agent is a nucleotide or a nucleotide analog. In certain aspects, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite anti-cancer agents for use in the present disclosure may be generally classified according to the metabolic process they affect, and can include, but are not limited to, analogues and derivatives of folic acid, pyrimidines, purines, and cytidine. Thus, in one aspect, the antimetabolite agent(s) is selected from the group consisting of cytidine analogs, folic acid analogs, purine analogs, pyrimidine analogs, and combinations thereof.

In one particular aspect, for example, the antimetabolite agent is a cytidine analog. According to this aspect, for example, the cytidine analog may be selected from the group consisting of cytarabine (cytosine arabinodside), azacitidine (5-azacytidine), and salts, analogs, and derivatives thereof.

In another particular aspect, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain aspects, for example, the folic acid analog may be selected from the group consisting of denopterin, methotrexate (amethopterin), pemetrexed, pteropterin, raltitrexed, trimetrexate, and salts, analogs, and derivatives thereof.

In another particular aspect, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain aspects, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-aminofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular aspect, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain aspects, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidin-2'-ene, 3'-deoxy-3'-deoxythymidin-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one aspect, the pyrimidine analog is other than 5-fluorouracil. In another aspect, the pyrimidine analog is gemcitabine or a salt thereof.

In certain aspects, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other aspects, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular aspect, the antimetabolite agent is other than 5-fluorouracil. In a particularly preferred aspect, the antimetabolite agent is gemcitabine or a salt or thereof (e.g., gemcitabine HCI (Gemzar®)).

Other antimetabolite anti-cancer agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

In one aspect, the antimitotic agent is a microtubule inhibitor or a mictrotubule stabilizer. In general, microtubule stabilizers, such as taxanes and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the vinca alkaloids, which prevent microtubule assembly, the microtubule stabilizers, such as taxanes, decrease the lag time and dramatically shift the dynamic equilibrium between tubulin dimers and microtubule polymers towards polymerization. In one aspect, therefore, the microtubule stabilizer is a taxane or an epothilone. In another aspect, the microtubule inhibitor is a vinca alkaloid.

One element of the combination therapy described herein includes the use of a taxane or derivative or analog thereof. The taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, Taxus brevifolia, and which have activity against certain tumors, particularly breast and ovarian tumors. In one aspect, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Atta-ur-Rabman, P. W. le Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, Mo.

Alternatively, the antimitotic agent can be a microtubule inhibitor; in one preferred aspect, the microtubule inhibitor is a vinca alkaloid. In general, the vinca alkaloids are mitotic spindle poisons. The vinca alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain aspects, for example, the vinca alkaloid is selected from the group consisting of vinblastine, vincristine, vindesine, vinorelbine, and salts, analogs, and derivatives thereof.

The antimitotic agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain aspects, the antimitotic anti-cancer agent is selected from the group consisting of taxanes, epothilones, vinca alkaloids, and salts and combinations thereof. Thus, for example, in one aspect the antimitotic agent is a taxane. More preferably in this aspect the antimitotic agent is paclitaxel or docetaxel, still more preferably paclitaxel. In another aspect, the antimitotic agent is an epothilone (e.g., an epothilone B analog). In another aspect, the antimitotic agent is a vinca alkaloid.

In certain aspects, the cancer drug refers to a medicament that may be used to treat cancer, and generally has the ability to kill cancerous cells directly. Examples of cancer drugs include, but are not limited to: thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as sunitimib and imatinib. Examples of additional cancer drugs include alkylating agents, antimetabolites, natural products, hormones and antagonists, and miscellaneous agents. Alternate names are indicated in parentheses. Examples of alkylating agents include nitrogen mustards such as mechlorethamine, cyclophosphainide, ifosfamide, melphalan sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, SFU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel, protein bound paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, rnedroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Alternate names and trade-names of these and additional examples of cancer drugs, and their methods of use including dosing and administration regimens, will be known to a person versed in the art.

According to certain aspects, the at least one additional anti-cancer agent is a chemotherapeutic agent. Suitable chemotherapeutic agents include, but are not limited to, alkylating agents, antibiotic agents, antimetabolic agents, hormonal agents, plant-derived agents and their synthetic derivatives, anti-angiogenic agents, differentiation inducing agents, cell growth arrest inducing agents, apoptosis inducing agents, cytotoxic agents, agents affecting cell bioenergetics i.e., affecting cellular ATP levels and molecules/activities regulating these levels, biologic agents, e.g., monoclonal antibodies, kinase inhibitors and inhibitors of growth factors and their receptors, gene therapy agents, cell therapy, e.g., stem cells, or any combination thereof.

According to these aspects, the chemotherapeutic agent is selected from the group consisting of cyclophosphamide, chlorambucil, melphalan, mechlorethamine, ifosfamide, busulfan, lomustine, streptozocin, temozolomide, dacarbazine, cisplatin, carboplatin, oxaliplatin, procarbazine, uramustine, methotrxate, pemetrexed, fludarabine, cytarabine, fluorouracil, floxuridine, gemcitabine, capecitabine, vinblastine, vincristine, vinorelbine, etoposide, paclitaxel, docetaxel, doxorubicin, daunorubicin, epirubicin, idarubicin, mitoxantrone, bleomycin, mitomycin, hydroxyurea, topotecan, irinotecan, amsacrine, teniposide, erlotinib hydrochloride and combinations thereof. Each possibility represents a separate aspect of the invention.

According to certain aspects, the at least one additional agent is a biologic drug, particularly an antibody. According to some aspects, the antibody is selected from the group consisting of cetuximab, anti-CD24 antibody, panitumumab and bevacizumab.

According to certain aspects, the additional anti-agent cancer is known to be effective in treating a particular type of cancer.

According to some aspects, the cancer is gastrointestinal cancer and the at least one additional anti-cancer agent is selected from the group consisting of oxaliplatin (Eloxatin®), fluorouracil (5-FU), anti-CD24 antibody, cetuximab (Erbitux®), irinotecan, panitumumab (Vectibix®), cisplatin, S-1 (dihydropyrimidine dehydrogenase (DPD) inhibitory fluoropyrimidine) and bevacizumab (Avastin®). Each possibility represents a separate aspect of the present invention.

According to other aspects, the cancer is pancreatic cancer, and the at least one additional anti-cancer agent is selected from the group consisting of gemcitabine (Gemzar®), erlotinib hydrochloride (Tarceva®) or GemCap (a combination of gemcitabine and capecitabine), and humanized anti-CD24 monoclonal antibodies. Each possibility represents a separate aspect of the present invention.

According to yet additional aspects, the cancer is prostate cancer and the at least one additional anti-cancer agent is selected from the group consisting of cetuximab (Erbitux®), bevacizumab (Avastin®) and humanized anti-CD24 monoclonal antibody. Each possibility represents a separate aspect of the present invention.

The terms "combination therapy" or "combined treatment" or "in combination" as used herein denotes any form of concurrent or parallel treatment with at least two distinct therapeutic agents.

It should be understood that reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. The derivative or analog of the chemotherapeutic agent or moiety retains similar chemical and/or physical property (including, for example, functionality) of the chemotherapeutic agent or moiety.

Kits

The present disclosure provides kits that can simplify the administration of any agent described herein. An exemplary kit of the invention comprises any agent described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the ocular surface. The kit can also further comprise one or more additional agent described herein.

In one embodiment, the kit comprises a container containing an effective amount of an agent of the invention, including, for example, compound of Formula I, methotrexate or a pharmaceutically acceptable salt thereof and an effective amount of another therapeutic agent, such those described herein.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features, combinations, and sub-combinations are of utility and may be employed without reference to other features, combinations, and sub-combinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Materials and Methods

Materials

Chitosan (DD>75%, Mw 310,000-375,000 Da) and Polycaprolactone (Mn 80,000) were purchased from Sigma-Aldrich Inc. (St. Louis, Mo.). The Shirasu porous glass (SPG) membrane was obtained from SPG Technology Co. (Japan). Trifluoroacetic acid, HEPES sodium salt, glutaraldehyde, polyoxyethylene (5) nonylphenylether (CO-520), sorbitane monooleate (Span 80), and dimethyl sulfoxide (DMSO) were purchased from Sigma-aldrich Inc. (St. Louis, Mo.). Bovine serum album (BSA) and bevacizumab (Bevacizumab) were purchased from Fisher Scientific International Inc. (Hampton, NH). Bicinchoninic acid (BCA) protein assay kit and colorimetric 3-(4,5-dimethylthiazol-2-yl)-2,5-diphenyltetrazoliumbromide salt (MTT) assay were purchased from Thermo Fisher Scientific Inc. (Columbus, Ohio). 1,1,1,3,3,3-hexafluoro-2-propanol (HFP) was purchased from Oakwood Products Inc. (Estill, S.C.). Human retinal pigment epithelial cell line (ARPE-19 cells, CRL2302) and DMEM: F-12 medium were purchased from American Type Culture Collection (Rockville, Md.). Other reagents used were analytical grade.

Chitosan Microparticle Synthesis

The influence of chitosan solution formulation and experimental parameter on the size and dispersion of chitosan microparticles was studied in the experiment.

0.5% (w/v), 1% (w/v), and 1.5% (w/v) chitosan with high molecular weight in 3% (w/w) acetic acid/sodium acetate buffer solution was prepared in 8 mL glass vials with continuous stirring at 400 rpm overnight until all the chitosan dissolved in the solution. The pH was controlled above 4.0 by using acetic acid/sodium acetate buffer solution considering the acidic influence on the therapeutic outcome of bevacizumab. The bioactivity of bevacizumab was investigated in acetic acid/sodium acetate buffer solutions at pH 4, 5, 6 to determine the minimum pH of acetic acid/sodium acetate buffer solution which could still dissolve chitosan but not affect the bioactivity of bevacizumab. Bovine serum albumin (BSA) was used as a model protein therapeutic for the initial loading and release studies considering the expense of bevacizumab. The intrinsic electrophoretic motilities of both bevacizumab and BSA are negative at pH 7.4, so BSA is the ideal model protein to assess the device efficacy. BSA was dispersed into the chitosan solution just before the experiment to complete the drug loading, and the ratio of BSA to chitosan was 1:1.

A water-in-oil emulsion method was adopted to prepare the chitosan microparticles with and without Shirasu porous glass (SPG) membrane based on the previous studies (Wang, L, et al. J. Controlled Release 2005 106:62-75; Dubey, R R & Parikh, R H. AAPS Pharm. Sci. Tech. 2004 5:20). Ethyl acetate or light paraffin oil was selected as the oil phase and they were compared in both particle production and uniformity. The mixture of chitosan and BSA was introduced into a 5 mL BD syringe and extruded through a 22-gauge hypodermic needle into the oil phase mixing with 5% (v/v) Span 80 by using a single-syringe infusion pump (Cole-Parmer) with continuous stirring at specific speeds (600 rpm, 800 rpm, and 1000 rpm) using a digital overhead stirrer (IKA Eurostar 20) to achieve microparticles of different sizes.

To achieve homogenous 10 µm microparticles, the SPG membrane (DC05U) was used in the particle preparation. Similarly, the SPG direct connecter attached to the 5 mL BD syringe filled with chitosan and BSA solution was immersed in the oil phase. The syringe pump extruded the solution to the oil phase through the SPG membrane with continuous stirring at 500 rpm avoiding particle aggregation. The volume ratio of water phase and oil phase was controlled around 1:20 (Wang, L, et al. J. Controlled Release 2005 106:62-75). To avoid damage to the SPG membrane caused by the rapid solution extrusion, the feeding rate was set to 1 mL/h.

After 30 minutes of homogenization, the oil phase turned opaque and then glutaraldehyde was dropwise added to the mixture to fully crosslink chitosan for 1 hr. The molar ratio of aldehyde groups of glutaraldehyde to amino groups of chitosan was 1:1 (Wang, L, et al. J. Controlled Release 2005 106:62-75). The particles were collected by centrifugation at 4000 rpm for 10 min, and the broken particles were filtered out through Whatman filter paper under the reduced pressure. The particles were washed twice with petroleum ether and acetone respectively and finally freeze-dried at −80° C. and 0.0030 mbar. The microparticles were stored in the refrigerator (4° C.) until further use.

TABLE 1

Important P-Factors for optimization and their ranges for chitosan microparticles preparation

| | Chitosan solution formulation (w/v %) | | |
| --- | --- | --- | --- |
| | 0.5 | 1 | 1.5 |
| pH | 4.0 | 5.0 | 6.0 |
| Specific speeds (rpm) | 600 | 800 | 1000 |
| Oil phase | Ethyl acetate | Light paraffin oil | |

PCL Coated Chitosan Microparticle Synthesis

PCL coating was completed by the oil-in-water method developed by Paik et al (Paik, P & Zhang, Y. Nanoscale 2011 3:2215-2219) with minor modifications. 0.015 g PCL was dissolved in 7.5 mL acetone at 45° C. in the oil bath and then cooled to 30° C. 0.015 g chitosan particles were dispersed in 1.0 mL acetone to prepare the stock solution which was dropwise added into PCL solution with 0.1 mL/min feeding rate and stirred at 500 rpm for 20 min for homogeneity. Then, 50 µL CO-520 was added dropwise into the mixture and stirred for another 30 min. The water phase was prepared by 37.5 mL deionized water and 1.0 mL CO-520, which served as the non-ionic surfactant assisting polymer deposition by stabilizing the water-in-oil emulsion. The mixture of oil phase was slowly added dropwise with a feeding rate of 0.1 mL/min to the water phase with continuous stirring at 600 rpm for three hours. Large white chunks which were pure PCL deposited at the bottom were removed, and the PCL coated chitosan microparticles and small pure PCL nanoparticles were suspended in the water phase. The particles were collected by centrifugation at 4000 rpm for 10 min. The particles were washed with water and isopropanol to remove CO-520, resulting in a porous structure. The microparticles were then freeze-dried at −80° C. under 0.0030 mbar overnight and stored in the refrigerator (4° C.) for further characterization.

Morphological Characterization

The morphological characteristics of chitosan microparticles and PCL coated microparticles were examined by scanning electron microscopy (SEM) (FEI, Quanta 200). Lyophilized chitosan microparticles and PCL coated microparticles were attached to carbon tape placed on aluminum stub mounts. Then, microparticles were sputter-coated with a standard 20 nm layer of gold-palladium at room temperature to obtain conductivity. The morphological characteristics of both surfaces and cross section of bi-layered films were similar to that of microparticles. While preparing the cross-section samples, the films were immersed and fractured in liquid nitrogen to acquire the cross section of films to minimize damage.

Size and Surface Charge

The average sizes of chitosan microparticles and PCL coated chitosan microparticles were determined by measuring 100 particles in at least three SEM images using ImageJ (NIH). A zeta potential analyzer (Brookhaven, Nanobrook ZetaPALS) was used to characterize the surface charge of chitosan microparticles, PCL-coated chitosan microparticles, BSA-loaded chitosan microparticles, BSA-loaded PCL-coated chitosan microparticles, BSA, and bevacizumab. More specifically, 1.5 mg particles were dispersed in 1.5 mL deionized water to prepare the stock solution (pH=7, 25° C.). Each solution was measured in 10 cycles. Each measurement was run three times with different particle batches.

Drug Loading Efficacy and Release Profile

In vitro BSA release profiles from uncoated chitosan microparticles and coated chitosan microparticles were acquired as follows. 4 mg microparticles were diluted in 1 mL phosphate buffered saline (PBS) in a 1.5 mL centrifuge tube and incubated at 37° C. in a water bath. At 1 h, 3 h, 6 h, 12 h, 24 h, 3 days, 1 week, 2 weeks, 1 month, 2 months, 3 months, the centrifugation (4000 rpm, 10 min) was applied on the solution, and the supernatant was collected. Fresh 1.0 mL PBS was added to the particles and incubated after each collection. The 25 μL supernatant and 200 μL BCA working agent solution were added to each well. The well plate was vigorously shaken for 30 seconds and incubated at 37° C. for 30 minutes. The absorbance measurement was obtained using a micro-plate reader (SpectraMax M5) at 562 nm. The BSA release profile was compared with the standard curve to get a plot of BSA total release versus time. For drug loading efficiency, microparticles were dissolved in dimethyl sulfoxide (DMSO) and PBS. The BSA in the supernatant was quantified by the micro-plate reader similar to the method of acquiring the BSA release profile. The loading efficiency was calculated as BSA content in the microparticles divided by total mass of microparticles. Similarly, the bevacizumab release profile was characterized at 270 nm in the absorbance readout. The measurements from each experiment were done in triplicate.

Biocompatibility

In vitro cytotoxicity of chitosan microparticles with and without the PCL coatings was assessed by MTT [((3-(4,5-Dimethylthiazol-2-yl)-2,5-Diphenyltetrazolium Bromide)) assay conducted with human retinal pigmented epithelial (ARPE-19) cells. ARPE-19 cells were seeded in 48-well plates at a density of $4\times10^4$ cells/well one day before adding microparticles. Cells were incubated with chitosan microparticles or PCL coated chitosan microparticles at concentrations of 0 (control group), 1, 10, and 100 mg/mL for 24 hours at 37° C. and 5% $CO_2$. Then, cell culture media was aspirated, and the cells were treated with 5 mg/mL MTT reagent in PBS (10 μL per 100 μL medium). Following incubation for 2 h at 37° C., 20 μL of DMSO was added to dissolve the formazan crystals formed in the well. The absorbance measurement of the formazan crystals was obtained by the micro-plate reader (SpectraMax, M5) at 570 nm. The control group was used to assess the cell viability of microparticles. All experiments were repeated 3 times.

Results

Chitosan Microparticles

The chitosan cores were first prepared using water-in-oil emulsion without the SPG membrane. To control the particle size around 10 μm for a higher drug payload, we optimized chitosan concentration (0.5% (w/v), 1.0% (w/v), 1.5% (w/v)), feeding rate (1.0 mL/h, 1.5 mL/h, 2 mL/h), stirring rate (600 rpm, 800 rpm, and 1000 rpm), and oil phase (ethyl acetate, light paraffin oil). The concentration of chitosan solution was found to be closely related to the solution viscosity. Higher viscosity made the solution more difficult to pass through the 21-gauge needle and form droplets in the oil phase. However, a lower viscosity led to a fast collapse of the water droplet in the oil phase as well as disturbed the microsphere formation. Smaller sized and broken chitosan microparticles (FIG. 1A) coexist with spherical and integrated chitosan microparticles (FIG. 1B). Accordingly, 1.0% (w/v) chitosan solution was selected for future experiments.

Figures 2A, 2B:
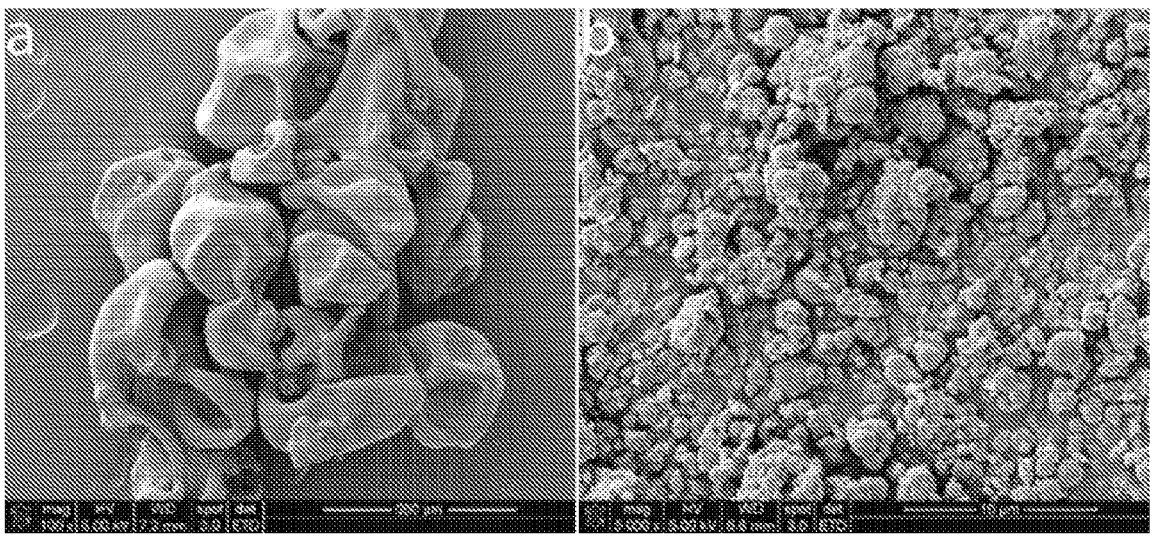
FIGS. 2A to 2D are SEM micrographs of chitosan MP in Ethyl acetate at 100 rpm (FIG. 2A), light paraffin oil at 1000 rpm (FIG. 2B), light paraffin oil at 800 rpm (FIG. 3C), and light paraffin oil at 600 rpm (FIG. 2D).
Figures 2C, 2D:
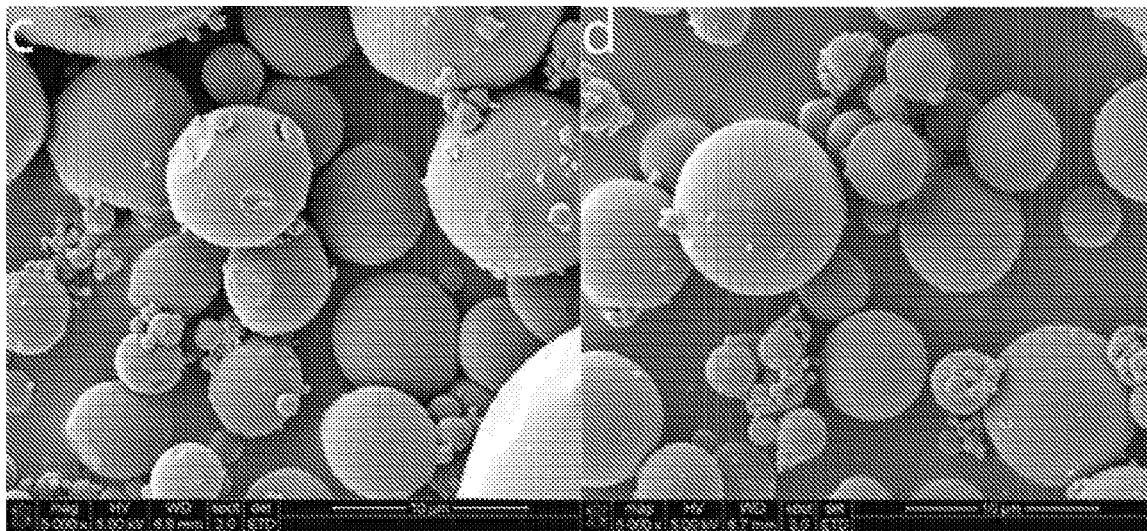

After optimizing the chitosan concentration, the effects of oil phase and stirring speed on particle size and polydispersity were studied. The SEM photographs of chitosan microparticles prepared with different parameters are shown in FIG. 2. As compared to the particles prepared in ethyl acetate with a diameter over 300 μm (FIG. 2A), small droplets were formed in light paraffin oil (FIGS. 2B, 2C, 2D) due to a more stable elastic interface between the water and oil phase. The primary emulsion was prepared under the following condition: 1 mL of aqueous phase in 20 ml of oil was dispersed by stirring at 1000 rpm. The stirring rate of 800 rpm was smaller than that of the previous emulsification (1000 rpm). We found that the particles are approximately 10 μm with some nano-sized particles surrounding. When the stirring rate was set at 600 rpm, no significant morphological differences between the chitosan microparticles prepared at 800 rpm and 600 rpm were observed. The chitosan microparticles have the spherical shape and the surface is smooth with nanoparticles adhering to the surface of chitosan microparticles (FIGS. 2C, 2D). High agitation rate leads to the formation of smaller polymerized globules and avoids water phase agglomeration (Sahil, K, et al. Int. J. Res. Pharm. Chem 2011 1:1184-1198), so the increase in stirring rate results in production of smaller sized chitosan particles (Jeffery, H, et al. Int. J. Pharm. 1991 77:169-175). However, the chitosan microparticles prepared at 600 rpm could not keep the size distribution constant due to the relatively high viscosity of light paraffin oil (Bouchemal, K, et al. Int. J. Pharm. 2004 280:241-251; R. Pal, A novel method to correlate emulsion viscosity data, Colloids Surf. A: Phys. Chem. Eng. Asp., 1998 137:275-286). The chitosan microparticles prepared under these conditions ranged from 1 μm to 15 μm. Moreover, the broad size distribution of chitosan microparticles may add difficulties in the following step of coating with PCL.

Figures 3A, 3B:
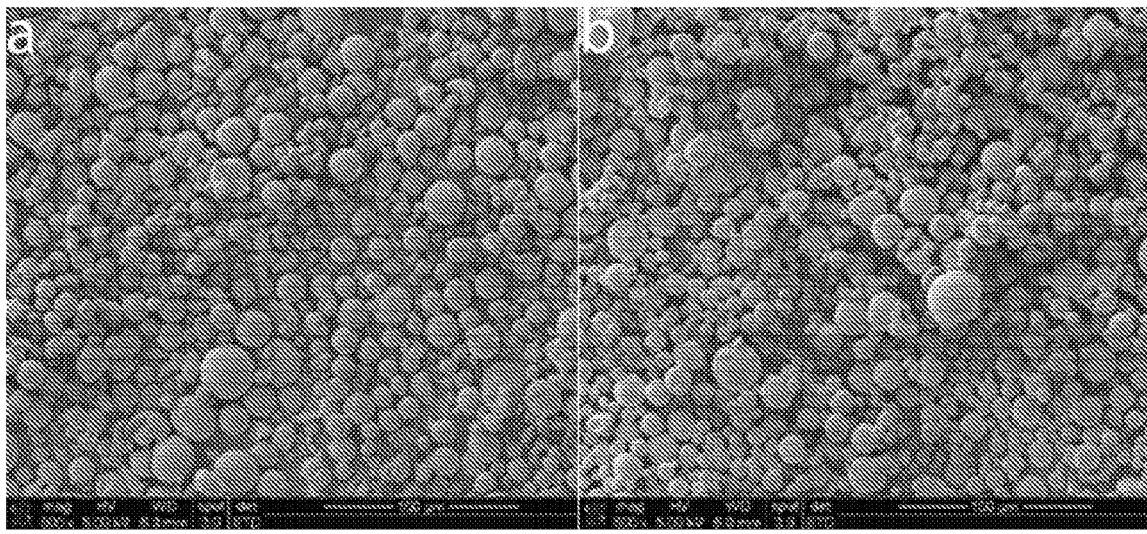
FIGS. 3A and 3B are SEM micrographs of chitosan microparticles 1.0% (w/v) (FIG. 3A) and 1.5% (w/v) (FIG. 3B).

To reduce the polydispersity of chitosan microparticles prepared by the mechanical stirring method, SPG membrane-based microparticle preparation was adopted. SPG membrane enables the water phase passing through numerous porous glass membrane and generates monodispersed emulsion. The size of chitosan microparticles mainly depends on the pore size of the membrane rather than stirring rate. FIG. 3 is the SEM image of chitosan microparticles prepared using the SPG membrane. The particles tend to be more uniform and integrated. Some broken particles appear in FIG. 3A, which were prepared using 1.0% (w/v) chitosan solution, but the particles are still 9.59±3.53 μm, as expected. More integrated particles were formed using 1.5% (w/v) chitosan solution since higher pressure was generated when the syringe pump extruded chitosan solution through the SPG membrane and it lowered the viscosity of the solution.

PCL Coated Chitosan Microparticle

Figures 4A, 4B:
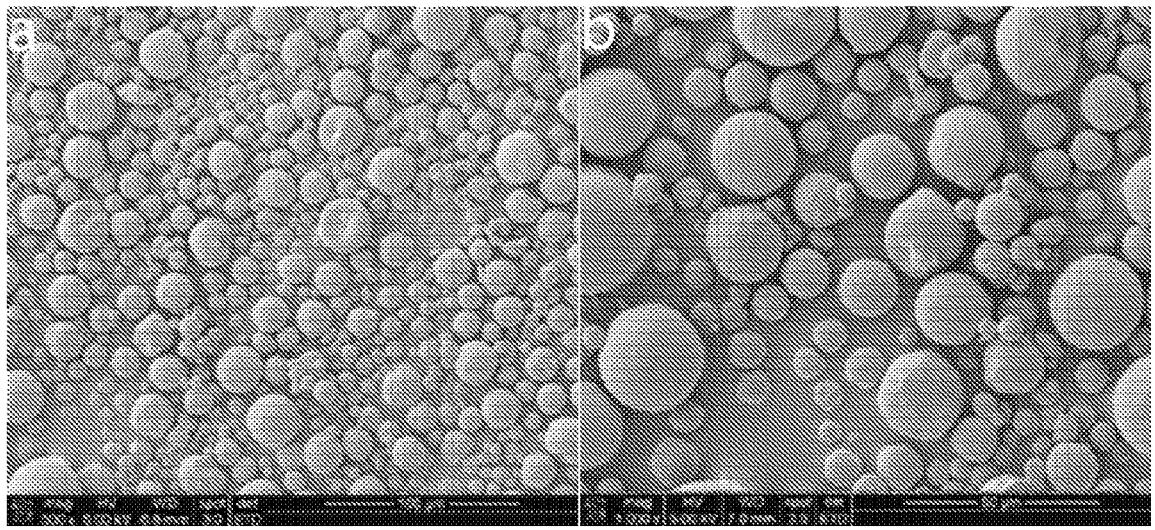
FIGS. 4A to 4C are SEM micrographs of PCL-coated chitosan MP under different magnifications 500× (FIG. 4A), 1000× (FIG. 4B), and 5000× (FIG. 4C).
Figure 4C:
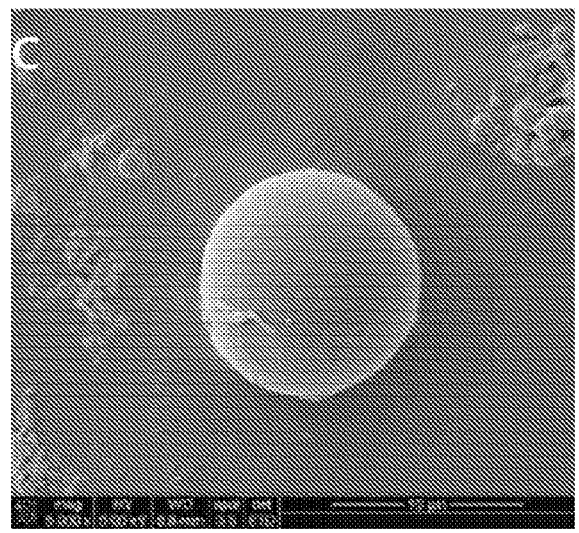
Figure 5A:
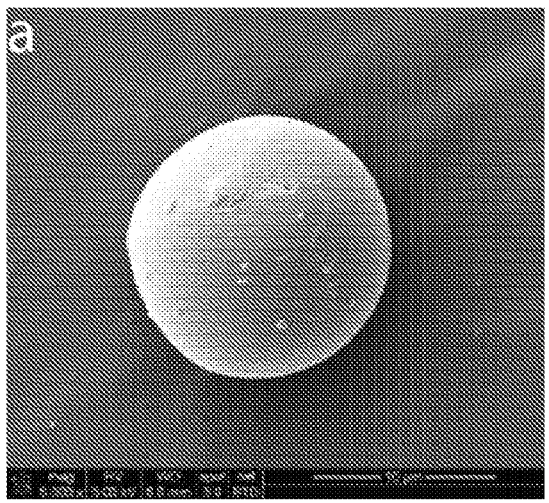
FIGS. 5A to 5F are SEM images of chitosan microparticle under different magnification 5000× (FIG. 5A), 20000× (FIG. 5B), 40000× (FIG. 5C), and PCL coated chitosan microparticle under different magnification 5000× (FIG. 5D), 20000× (FIG. 5E), and 40000× (FIG. 5F).
Figure 5B:
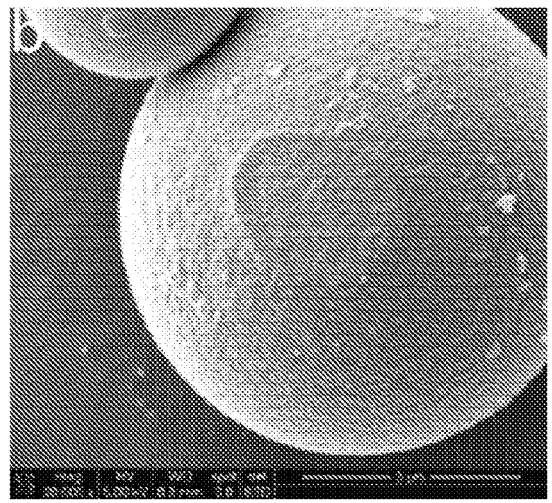
Figure 5C:
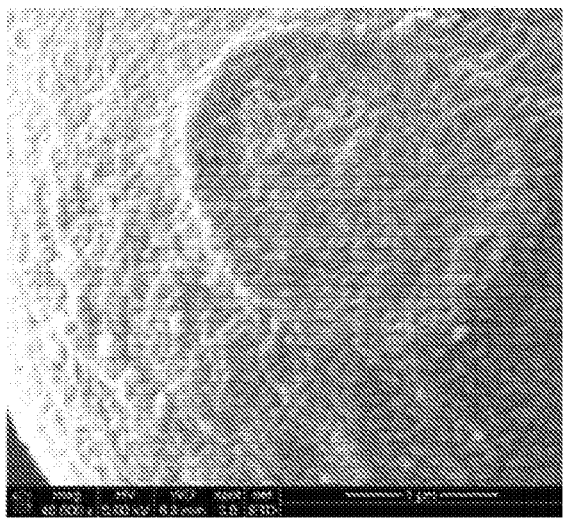
Figure 5D:
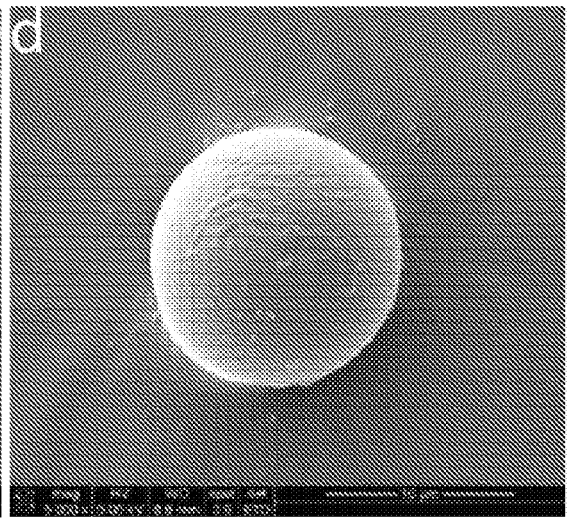
Figures 5E, 5F:
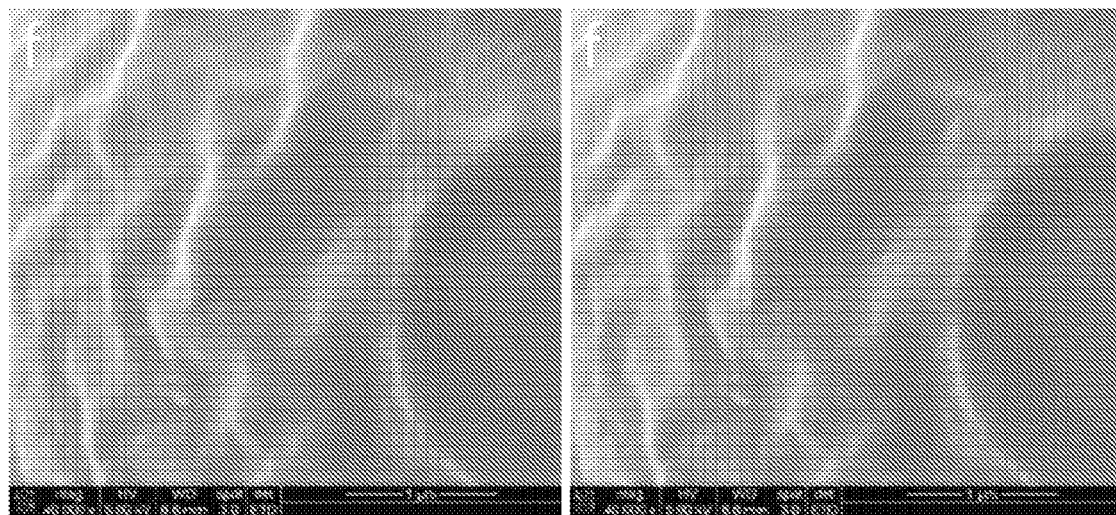

Coating PCL on the chitosan microparticles was similar to the preparation of chitosan microparticles in the method section but the oil-in-water emulsification was used instead. SEM micrographs presented in FIG. 4 show that the secondary emulsion formulation produces PCL-coated chitosan microparticles with different surface morphologies. Most particles are larger than 10 μm and a few pure PCL nanoparticles coexist in the image due to the excess PCL polymer in the oil phase. The average diameter of PCL coated microparticles is 12.51±5.86 μm. There is no significant increase in diameter of PCL-coated chitosan microparticles as compared to the chitosan cores.

Morphology of Microparticles

Figure 11A:
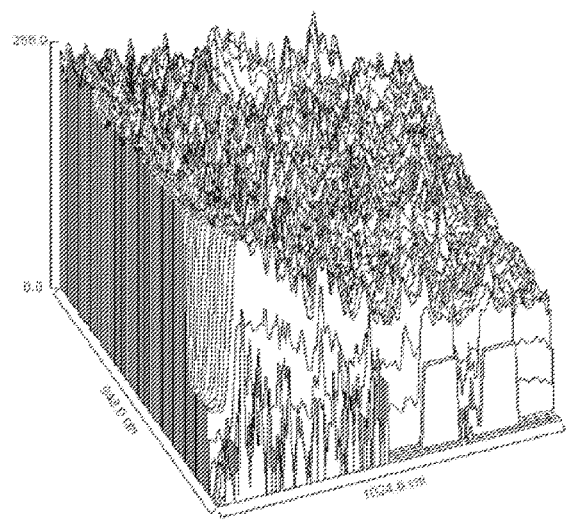
FIGS. 11A-11B show surface plates corresponding to SEMS images of chitosan microparticles (FIG. 11A) and PCL coated chitosan microparticles (FIG. 11B).
Figure 11B:
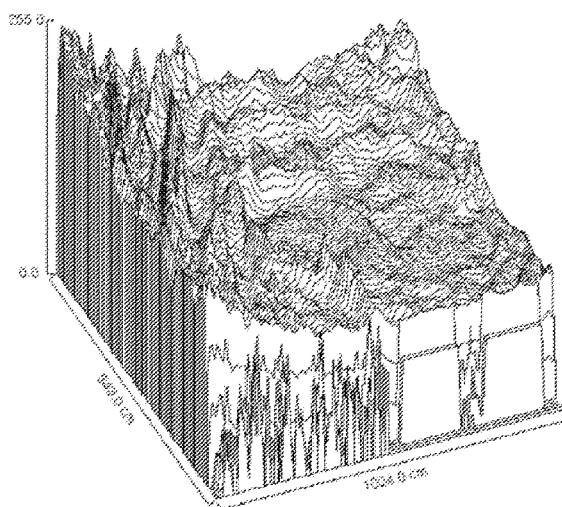

FIG. 5 shows the SEM image of chitosan microparticles and PCL-coated chitosan microparticles. Chitosan microparticles are spherical and have relatively rough surfaces. At higher magnification, FIG. 5C shows the same spherical microparticles with a rough surface, which is consistent with previous literature reports (Ko, J A, et al. Int. J. Pharm. 2002 249:165-174). After coating the chitosan core with a PCL shell, the high magnification in FIG. 5C reveals that a thin layer of PCL covers the microparticles surface and the PCL coated microparticle surface is slightly smoother with grooves as compared to the chitosan core. This change of surface morphology of microparticles is indicative of successful PCL coating, based on previous SEM images and PCL nano- and micro-structure. The surface plots of chitosan microparticle and PCL coated chitosan microparticle are shown in the FIGS. 11A and 11B, respectively. This change of surface morphology is indicative of successful PCL coating.

Surface Charge

Zeta potential of microparticles was measured (Table 2) at physiological pH (pH=7.4). There was a significant decrease in the surface charge from 20.14 mV to 0.1375 mV after secondary emulsion since the free amine ions were covered by PCL shell. However, after loading with bovine serum albumin (BSA), the zeta potential became negatively charged due to the negative isoelectric point of BSA which facilitates the movement in the vitreous humor filled with negatively charged hyaluronic gel. Overall, the zeta potential decreased after coating with PCL which revealed the core-shell structure of the microparticles.

TABLE 2

Zeta potentials of chitosan and PCL coated microparticles with and without BSA.

| Microparticle Type | Zeta Potential (mv) |
|---|---|
| Chitosan microparticles | +21.12 |
| PCL coated chitosan microparticles | +0.125 |
| Chitosan microparticles loaded with 50%(w/w) BSA | −20.98 |
| PCL coated chitosan microparticle loaded with 50%(w/w) BSA | −0.178 |
| BSA | −24.41 |
| Bevacizumab | −4.03 |

Cytotoxicity

Figure 6:
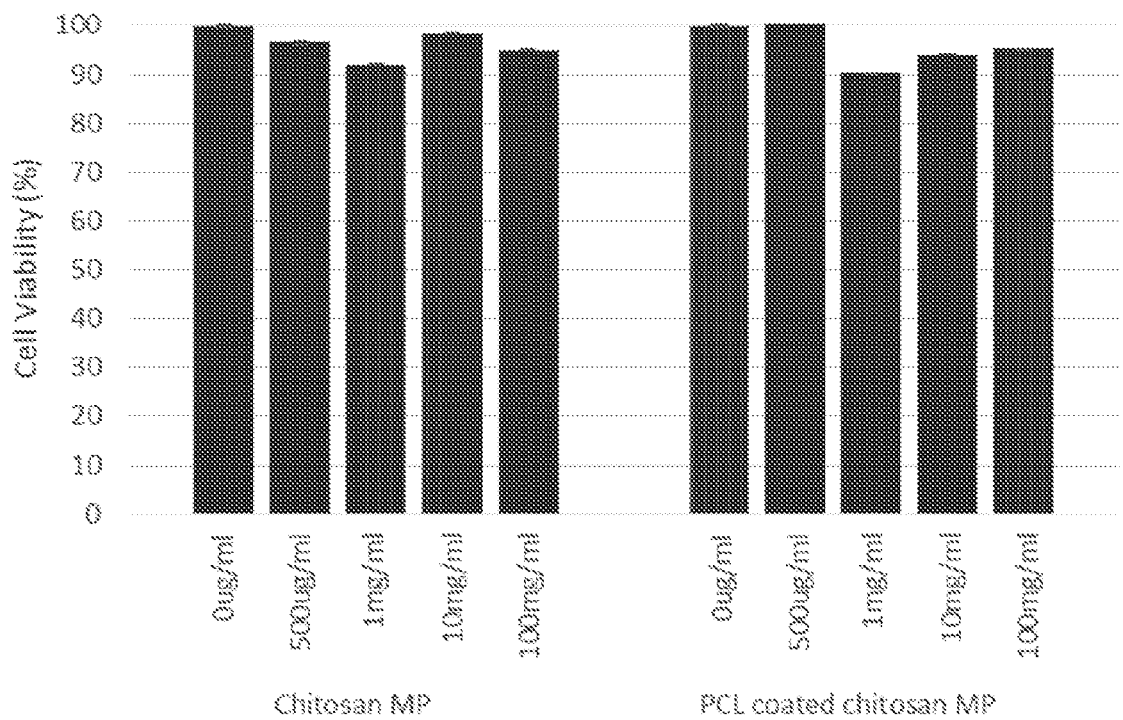
FIG. 6 shows in vitro cytotoxicity of microparticles.
Figure 7:
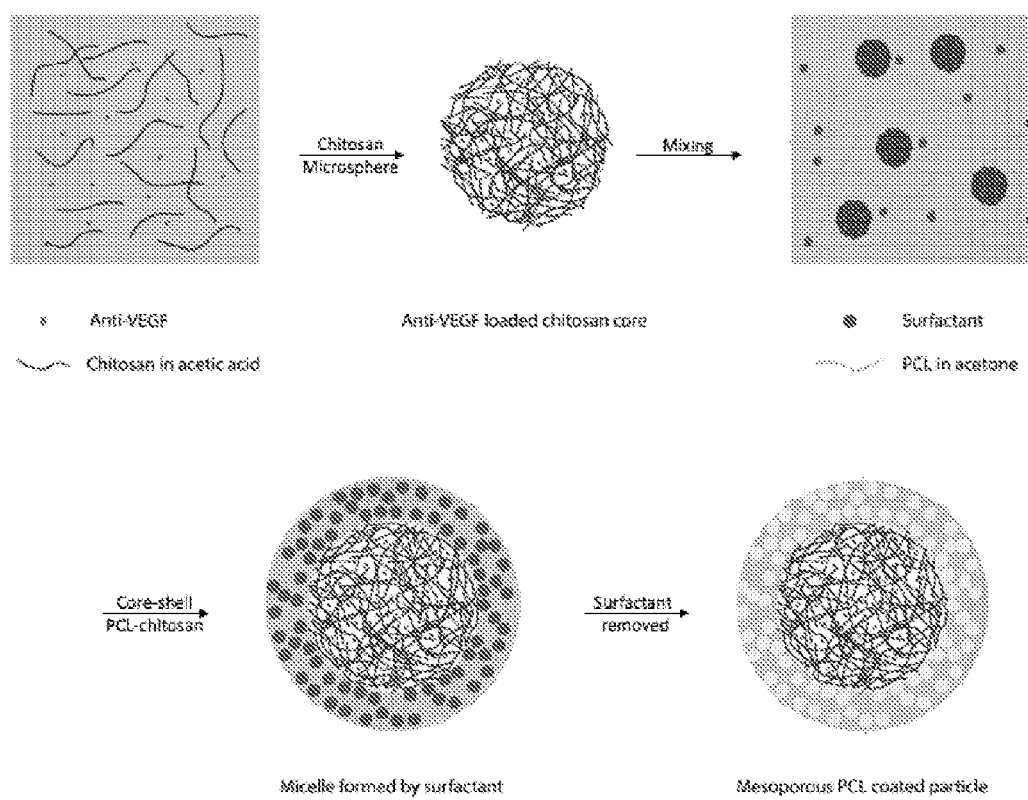
FIG. 7 shows a scheme of an aspect core-shell microparticle synthesis.

ARPE-19 cells were used to assess the toxicity of microparticles in this study. The cells were incubated with microparticles for 24 h. The cell viability was measured to be greater than 90% at all concentrations tested as shown in FIG. 6. These data suggest that the cell vialability is independent on the concetration of microparticles. Also, there is no significant difference on cell density in the medium containing chitosan microparticles or PCL coated chitosan microparticles. Microparticles demonstrated minimal toxicity to the ARPE-19 cells, indicating potnetial for biomedical application in the eye.

TABLE 3

Zeta Potential of Bevacizumab in PBS.

| Run | Mobility | Zeta Potential (mV) |
|---|---|---|
| 1 | −0.45 | −6.07 |
| 2 | +0.56 | +7.59 |
| 3 | −0.08 | −1.15 |
| 4 | −0.67 | −9.03 |
| 5 | +0.13 | +1.80 |
| 6 | +0.17 | +2.35 |
| 7 | −0.08 | −1.13 |
| 8 | −0.89 | −1.21 |
| 9 | −0.61 | −8.30 |
| Mean | −0.30 | −4.03 |
| Std Error | 0.17 | 2.32 |
| Combined | −0.23 | −4.01 |

TABLE 4

Zeta Potential of Bevacizumab in distilled water.

| Run | Mobility | Zeta Potential (mV) |
|---|---|---|
| 1 | −0.42 | −5.66 |
| 2 | −0.78 | −10.61 |
| 3 | −0.59 | −7.95 |
| 4 | +1.01 | +13.71 |
| 5 | +0.91 | +12.24 |
| 6 | +0.45 | +6.06 |
| 7 | +1.19 | +16.13 |
| 8 | +0.39 | +5.33 |
| 9 | +0.36 | +4.80 |
| Mean | +0.27 | +3.69 |
| Std Error | 0.22 | 2.92 |
| Combined | +0.22 | +2.95 |

Example 2

Preparation of Chitosan Microparticles

A water-in-oil emulsion method was adopted to prepare chitosan microparticles with Shirasu porous glass (SPG) membrane based on the previous studies with some modifications [14,15]. 0.5% (w/v), 1% (w/v), and 1.5% (w/v) chitosan dissolved in pH 4.5 acetic acid/sodium acetate buffer solutions with different pH values were prepared in 8 mL glass vials with continuous stirring overnight until all the chitosan dissolved in the solution. The pH was controlled above 4.0 to avoid an acidic environment which may influence the therapeutic outcome of bevacizumab. Bovine serum albumin (BSA) was used as a model protein therapeutic for the some loading and release studies as a protein surrogate for bevacizumab. BSA was directly dispersed into the chitosan solution before the preparation of microparticles to complete drug loading, and the ratio of BSA to chitosan was 1:1. The chitosan solution loaded with BSA was introduced into a 5 mL BD syringe and extruded through SPG membrane into the oil phase. The mixture of liquid paraffin and petroleum ether 7:5 (v/v) containing 4 wt % Span® 80 (non-ionic surfactant, CAS No. 1338-43-8; Sigma-Aldrich) was injected by using a single-syringe infusion pump (Cole-Parmer) with continuous stirring at 300 rpm avoiding particle aggregation. The volume ratio of the water phase and oil phase was 1:10. After 30 minutes of homogenization, glutaraldehyde was dropwise added to the emulsion to fully crosslink chitosan for 1 hour. The molar ratio of aldehyde groups of glutaraldehyde to amino groups of chitosan was 1:1. The particles were then collected by centrifugation at 1000 rpm, and the broken particles were filtered out under the reduced pressure. The particles were washed twice with petroleum ether and acetone respectively and finally freeze-dried and stored in the fridge.

Preparation of PCL-Coated Chitosan Microparticles

PCL coating was completed by the oil-in-water method developed by Paik et al. [16] with minor modifications. 0.015 g PCL was dissolved in 7.5 mL acetone at 45° C. in the oil bath and then cooled to 30° C. 0.015 g chitosan particles were dispersed in 1.0 mL acetone to prepare the stock solution which was dropwise added into PCL solution with 0.1 mL/min feeding rate and stirred at 500 rpm for 20 min to achieve homogeneity. Then, 50 µL CO-520 (IGEPAL® CO-520; Sigma-Aldrich) was added dropwise into the mixture and stirred for another 30 min. The water phase was prepared by 37.5 mL deionized water and 1.0 mL CO-520, which served as the non-ionic surfactant assisting polymer deposition by stabilizing the water-in-oil emulsion. The oil phase was slowly added dropwise with a feeding rate of 0.1 mL/min to the water phase with continuous stirring at 600 rpm for three hours. PCL coated chitosan microparticles were collected by centrifugation at 1000 rpm. The particles were washed with water and isopropanol and then freeze-dried.

PCL-coated chitosan microparticles comprising BSA or bevacizumab were prepared as described above, but using a mass ratio of BSA or bevacizumab to chitosan of 1:1. Briefly, the chitosan core was prepared as describe above using a 1% (w/v) chitosan solution (high molecular weight), pH 4.5 adjusted using acetic acid/sodium acetate buffer solution) and BSA or bevacizumab (mass ratio of chitosan to drug 1:1). The surface of chitosan core was crosslinked by glutaraldehyde. The molar ratio of aldehyde groups of glutaraldehyde to amino groups of chitosan was 1:1. The emulsifier, Span 80, was removed from the particles following centrifugation. The shell was prepared using PCL as described above, and the emulsifier, CO-520 (IGEPAL® CO-520, Sigma-Aldrich) was removed from the particles following centrifugation. The incorporation efficiency of the BSA into the microparticle was as follows: 127.70±20.31 µg BSA per 2 mg micropaticles. The incorporation efficiency of the Bevacizumab into the microparticle was as follows: 151.91±24.02 µg Bevacizumab per 2 mg micropaticles.

Determination of Release of BSA or Bevacizumab from Microparticles

In vitro BSA release profiles from uncoated chitosan microparticles and coated chitosan microparticles were acquired as following procedure. Microparticles were diluted in 1.0 mL phosphate buffered saline (PBS) in a 1.5 mL Eppendorf tube and maintained at 37° C. in a water bath. At 30 min, 1 h, 3 h, 6 h, 12 h, 24 h, 2 days, 4 days, 1 week, 2 weeks, 1 month, 2 months, 3 months, the centrifugation (1000 rpm, 10 min) was applied on the solution, and the supernatant was collected. Fresh 1.0 mL PBS was added to the particles and incubated after each collection. The 25 µL supernatant and 200 µL BCA working agent solution were added to each well. The well plate was vigorously shaken for 30 seconds and incubated at 37° C. for 30 minutes. The absorbance measurement was obtained using a micro-plate reader (SpectraMax M5) at 562 nm. The BSA release profile was compared with the standard curve to get a plot of BSA total release versus time. For drug loading efficiency, microparticles were dissolved in dimethyl sulfoxide (DMSO) and PBS. The BSA in the supernatant was quantified by the micro-plate reader similar to the method of acquiring the BSA release profile. The loading efficiency was calculated as BSA content in the microparticles divided by total mass of microparticles. Similarly, the bevacizumab release profile was characterized by absorbance at 277 nm. The measurements from each experiment were done in triplicate.

For determination of the release of bevacizumab, microparticles were diluted in 1.0 mL phosphate buffered saline (PBS) in a 1.5 mL Eppendorf tube and maintained at 37° C. in a water bath. At 30 min, 1 h, 3 h, 6 h, 12 h, 24 h, 2 days, 4 days, 1 week, 2 weeks, 1 month, 2 months, 3 months, the centrifugation (1000 rpm, 10 min) was applied on the solution, and the supernatant was collected. Fresh 1.0 mL PBS was added to the particles and incubated after each collection. The 200 µL supernatant was added to each well. The bevacizumab release profile was characterized at 277 nm in the absorbance readout.

Results

Figure 8:
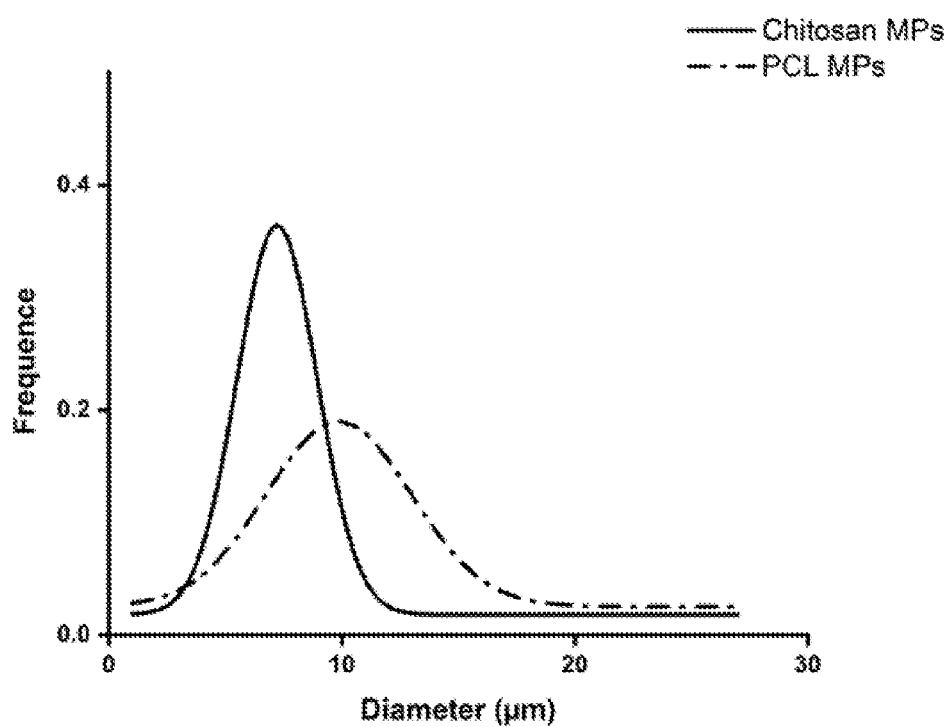
FIG. 8 shows the size distribution for chitosan microparticles (in the figure labeled as "Chitosan MPs") and PCL coated chitosan microparticles (in the figure labeled as "PCL MPs").

As shown in FIG. 8, the chitosan microparticles ranged from 6 µm to 12 µm. The average diameter of the chitosan microparticle was 8.78±3.45 µm. After PCL coating, the diameter of PCL coated chitosan microparticle was increased to 12.66±5.87 µm on average with wider size distribution. By comparing the diameter of each peak, it is believed that the thickness of PCL layer was approximately 1-1.5 µm.

Zeta potential of microparticles was measured (Table 5) at physiological pH (pH=7.4). There was a significant decrease in the surface charge from 20.14 mV to 0.1375 mV after secondary emulsion since the free amine ions were covered by PCL shell. However, after loading with bovine serum albumin (BSA), the zeta potential became negative due to the negative isoelectric point of BSA. Without wishing to be bound by a particular theory, it is believed that the observed zeta potential can facilitate the movement in the vitreous humor filled with negatively charged hyaluronic acids. Overall, the data show that the zeta potential decreased after coating with PCL which revealed the core-shell structure of the microparticles.

TABLE 5

Zeta potential of microparticles.

| Microparticle type | Zeta potential (mv) |
| --- | --- |
| Chitosan microparticles | +25.48 ± 1.64 |
| PCL coated microparticles | +0.12 ± 0.62 |
| Chitosan microparticles loaded with BSA | −20.98 ± 1.42 |
| PCL coated microparticles loaded with BSA | −0.18 ± 0.071 |
| BSA | −24.41 ± 1.39 |
| Bevacizumab | −4.01 ± 2.31 |

Figure 9:
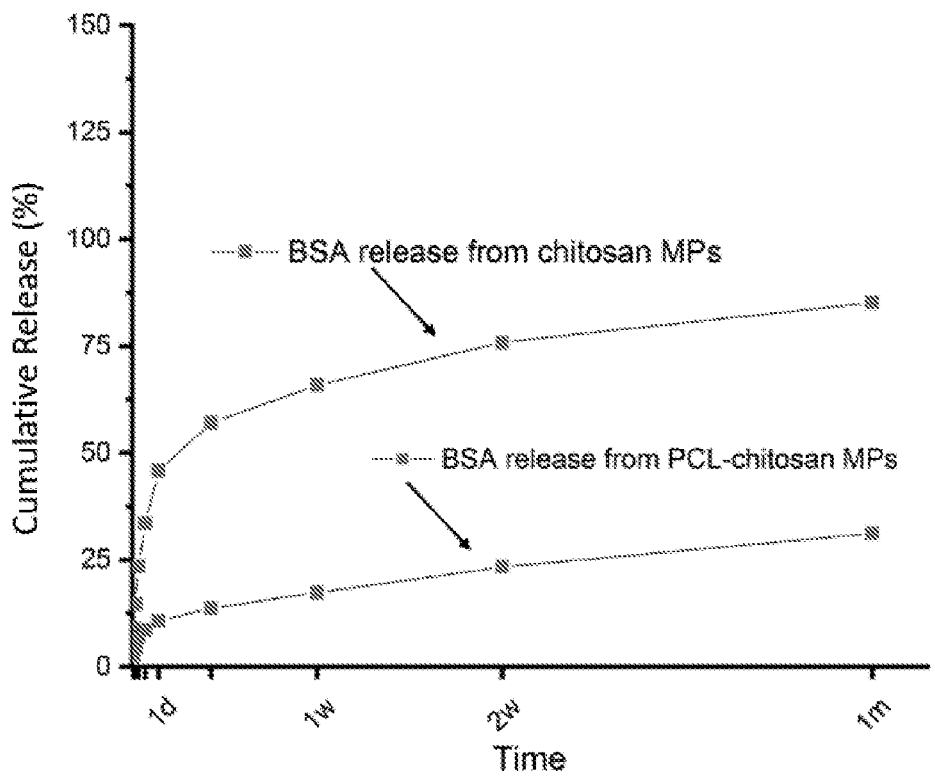
FIG. 9 shows data for the cumulative release of BSA from chitosan microparticles (in the figure labeled as "Chitosan MPs") and PCL coated chitosan microparticles (in the figure labeled as "PCL-chitosan MPs") over time.
Figure 10:
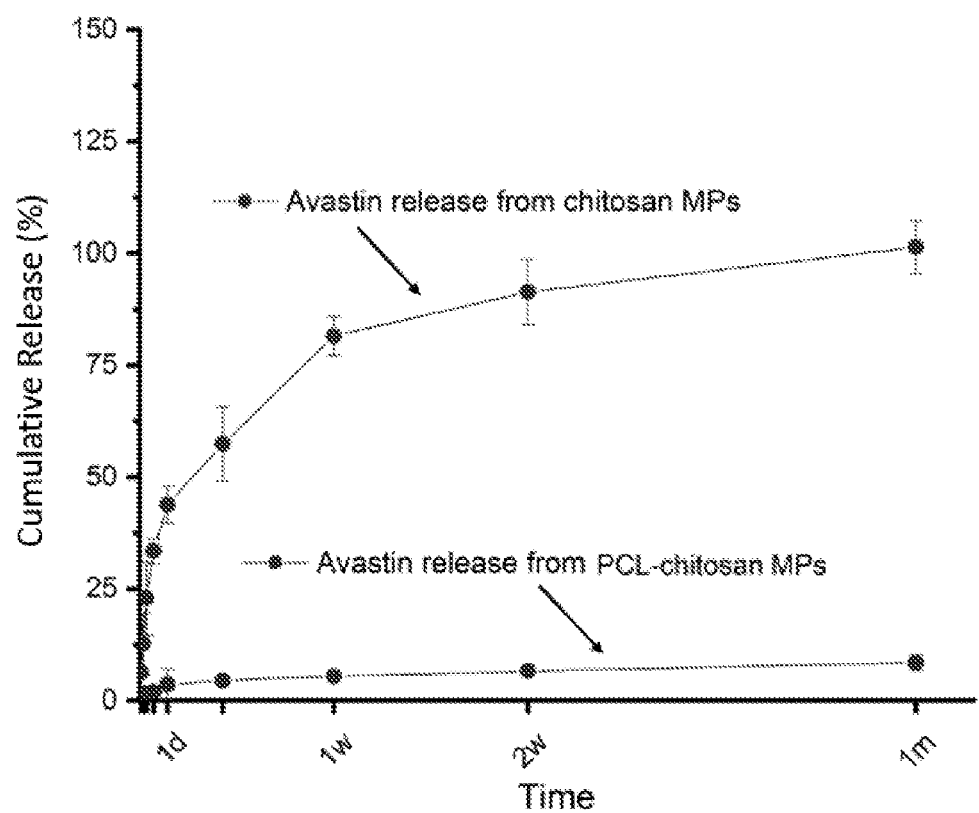
FIG. 10 shows data for the cumulative release of bevacizumab from chitosan microparticles (in the figure labeled as "Chitosan MPs") and PCL coated chitosan microparticles (in the figure labeled as "PCL-chitosan MPs") over time.

The release of BSA from PCL-coated microparticles is shown in FIG. 9, and the release of bevacizumab from the PCL-coated microparticles is shown in FIG. 10.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A drug delivery composition comprising particles having:
   a core component comprising a therapeutic agent and a first polymer having a net positive charge under physiological conditions, wherein the first polymer comprises a chitosan or derivative thereof, and wherein the therapeutic agent comprises an anti-VEGF therapeutic; and
   a shell layer comprising a second polymer that is biodegradable under physiological conditions, wherein the second polymer comprises poly (ε-caprolactone);
   wherein the drug delivery composition is suitable for injection into an eye of a subject and wherein the amount of the therapeutic agent released after 30 days in phosphate-buffered saline at pH 7.4 is about 5% to about 50% of the amount of the therapeutic agent initially present.

2. The drug delivery composition of claim 1, wherein the chitosan or derivative thereof has a degree of deacetylation of about 60% to about 90%.

3. The drug delivery composition of claim 2, wherein the chitosan or derivative thereof has a degree of deacetylation of at least about 70%, at least about 75%, or at least about 80%.

4. The drug delivery composition of claim 1, wherein the first polymer has a molecular weight of about 50,000 Da to about 500,000 Da, of about 100,000 Da to about 400,000 Da, of about 100,000 Da to about 400,000 Da, of about 200,000 Da to about 400,000 Da, of about 300,000 Da to about 400,000 Da, or of about 310,000 Da to about 375,000 Da.

5. The drug delivery composition of claim 1, wherein the particles have a size range of about 50 nm to about 100 μm, of about 1 μm to about 50 μm, of about 5 μm to about 20 μm, of about 1 μm to about 15 μm, of about 2 μm to about 15 μm, of about 3 μm to about 15 μm, of about 4 μm to about 15 μm, of about 5 μm to about 15 μm, or of about 50 nm to about 1 μm.

6. The drug delivery composition of claim 1, wherein the particles have a size range of about 50 nm to about 100 μm, of about 1 μm to about 50 μm, of about 5 μm to about 20 μm, or of about 50 nm to about 1 μm; and wherein the shell layer has a thickness of about 10 nm to about 1 μm or of about 500 nm to about 1 μm.

7. The drug delivery composition of claim 1, wherein the shell layer comprises about 0.1 wt % to about 25 wt %, about 0.1 wt % to about 10 wt %, or about 0.1 wt % to about 5 wt % based on the total weight of the first polymer and the second polymer.

8. The drug delivery composition of claim 1, wherein the core component comprises about 75 wt % to about 99.9 wt %, about 90 wt % to about 99.9 wt %, or about 95 wt % to about 99.9 wt % based on the total weight of the first polymer and the second polymer.

9. The drug delivery composition of claim 1, wherein the therapeutic agent is present in the particle at about 0.1 wt % to about 75 wt %, about 30 wt % to about 60 wt %, or about 45 wt % to about 55 wt % based on the total weigh of the first polymer, the second polymer, and the therapeutic agent.

10. The drug delivery composition of claim 1, wherein a surface charge measured as a zeta potential at pH 7.4 has a value of about −25 mV to about 25 mV, of about −20 mV to about 20 mV, of about −15 mV to about 15 mV, of about −10 mV to about 10 mV, of about −7.5 mV to about 7.5 mV, of about −5 mV to about 5 mV, of about −4 mV to about 4 mV, of about −3 mV to about 3 mV, of about −2 mV to about 2 mV, of about −1 mV to about 1 mV, or of about −0.5 mV to about 0.5 mV.

11. The drug delivery composition of claim 1, wherein the anti-VEGF therapeutic is selected from bevacizumab, ranibizumab, lapatinib, sunitinib, sorafenib, axitinib, pazopanib, pharmaceutically acceptable salts thereof, and combinations thereof.

12. A method of treating an ophthalmological disorder, the method comprising injecting a therapeutically effective amount of the drug delivery composition of claim 1 into an eye of a subject.

13. The method of claim 12, wherein the ophthalmological disorder is acute macular neuroretinopathy; Behcet's disease; neovascularization; diabetic uveitis; histoplasmosis; infections; macular degeneration; edema; multifocal choroiditis; ocular trauma which affects a posterior ocular site or location; ocular tumors; retinal disorders; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, a cancer, and glaucoma.

14. The method of claim 12, wherein the injection is to the vitreous chamber of the eye.

15. The method of claim 12, wherein the injection is an intravitreal injection, a subconjunctival injection, a subtenon injection, a retrobulbar injection, or a suprachoroidal injection.

16. The method of claim 12, wherein the ophthalmological disorder is wet age-related macular degeneration (wet AMD), a cancer, neovascularization, macular edema, or edema.

17. The method of claim 12, wherein the ophthalmological disorder is wet age-related macular degeneration.

* * * * *